US010782286B2

(12) United States Patent
Braasch et al.

(10) Patent No.: US 10,782,286 B2
(45) **Date of Patent: *Sep. 22, 2020**

(54) ANTIGEN DETECTION OF TRICHINELLA

(71) Applicant: EUROIMMUN Medizinische Labordiagnostika AG, Luebeck (DE)

(72) Inventors: Jana Braasch, Luebeck (DE); Stefanie Ostermann, Rethwisch (DE); Monika Mackiewicz, Luebeck (DE)

(73) Assignee: EUROIMMUN Medizinische Labordiagnostika AG, Luebeck (DE)

( * ) Notice: Subject to any disclaimer, the term of this patent is extended or adjusted under 35 U.S.C. 154(b) by 0 days.

This patent is subject to a terminal disclaimer.

(21) Appl. No.: 16/841,728

(22) Filed: Apr. 7, 2020

(65) Prior Publication Data

US 2020/0232976 A1 Jul. 23, 2020

Related U.S. Application Data

(63) Continuation of application No. 16/225,007, filed on Dec. 19, 2018, now Pat. No. 10,663,460.

(30) Foreign Application Priority Data

Dec. 20, 2017 (EP) .................................... 17208994
Oct. 9, 2018 (EP) .................................... 18199404

(51) Int. Cl.

| | |
|---|---|
| ***G01N 33/53*** | (2006.01) |
| ***C07K 16/18*** | (2006.01) |
| ***C07K 14/435*** | (2006.01) |
| ***G01N 33/58*** | (2006.01) |
| ***G01N 33/487*** | (2006.01) |
| ***G01N 33/569*** | (2006.01) |
| ***G01N 33/12*** | (2006.01) |
| ***G01N 33/68*** | (2006.01) |

(52) U.S. Cl.

CPC ..... *G01N 33/5308* (2013.01); *C07K 14/4354* (2013.01); *C07K 16/18* (2013.01); *G01N 33/12* (2013.01); *G01N 33/48735* (2013.01); *G01N 33/569* (2013.01); *G01N 33/58* (2013.01); *G01N 33/6854* (2013.01); *G01N 2333/4353* (2013.01)

(58) Field of Classification Search

None

See application file for complete search history.

(56) References Cited

U.S. PATENT DOCUMENTS 4,613,568 A 9/1986 Pfeiffer
2012/0171711 A1 7/2012 Bauer

FOREIGN PATENT DOCUMENTS

DE 40 04 537 2/1991
WO 2006/034716 4/2006
WO 2010/146184 12/2010

OTHER PUBLICATIONS

Altschul et al., "*Basic Local Alignment Search Tool,*" J. Mol. Biol. (1990) 215, 403-410.

Altschul et al., "*Gapped BLAST and PSI-BLAST: a new generation of protein database search programs,*" Nucleic Acids Research., 1997, vol. 25, No. 17 3389-3402.

Appleton et al., "*Rapid expulsion of Trichinella spiralis in suckling rats: mediation by monoclonal antibodies,*" Immunology 1988 65 487-492.

BfR, [German Federal Institute for Risk Assessment], "*Ringversuch zum Nachweis von Trichinellen in Fleisch* (2016) [*Interlaboratory test for proof of Trichinella in meat*]," Robert Koch Insitut, pp. 1-15.

BfR, [German Federal Institute for Risk Assessment], "*Ringversuch zum Nachweis von Trichinellen in Fleisch* (2016) [*Interlaboratory test for proof of Trichinella in meat*]," Robert Koch Insitut, pp. 1-15, with English translation.

BfR, [German Federal Institute for Risk Assessment], "*Trichinellose—Erkennung, Behandlung und Verhütung,*" 2007, pp. 1-4.

BfR, [German Federal Institute for Risk Assessment], "*Trichinellose—Erkennung, Behandlung und Verhütung,*" 2007, pp. 1-4, with English Translation.

Chenna et al., "*Multiple sequence alignment with the Clustal series of programs*", Nucleic Acids Research, 2003, vol. 31, No. 13 3497-3500 DOI: 10.1093/nar.gkg500.

Dupouy-Camet et al., "*FAO/WHO/OIE Guidelines for the surveillance, management, prevention and control of trichinellosis,*" Food and Agriculture Org. of the U.N., World Health Org., World Org. for Animal Health, 2007, pp. 1-119.

European Union Reference Laboratory for Parasites, Report on the validation of the Trichin-L antigen test kit of the Bio-Rad company, 2010, pp. 1-16.

Kapel, "*Changes in the EU legislation on Trichinella inspection—New challenges in the epidemiology,*" Veterinary Parasitology, 132 (2005) 189-194 doi:10.1016/j.vetpar.2005.05.055.

Kornikova, K (Parasitology research, (Nov. 2006) vol. 99, No. 6, pp. 643-647).

(Continued)

*Primary Examiner* — Jennifer E Graser

(74) *Attorney, Agent, or Firm* — Grüneberg and Myers PLLC

(57) ABSTRACT

*Trichinella* can be detected in a tissue extract sample. A suitable kit includes (a) a detection carrier containing a first antibody against one or more antigens of *Trichinella*, and (b) (i) a second antibody against one or more antigens of *Trichinella*, wherein the second antibody is bound to a signal molecule, or (b) (ii) contains one or more antigens of *Trichinella* bound to a signal molecule, wherein the antigens of (b) (ii) are configured so as to dissolve binding of the antigens of (a) to the first antibody by competitive displacement.

8 Claims, 11 Drawing Sheets

Specification includes a Sequence Listing.

(56) References Cited

OTHER PUBLICATIONS

Liu et al., "*Trichinellosis in China: epidemiology and control,*" TRENDS in Parasitology vol. 18 No. 12 Dec. 2002 pp. 553-556.
Mitreva et al., "*Biology and genome of Trichinella spiralis,*" 2006, Wormbook, pp. 1-21 doi/10.1895/wormbook.1.124.1.
Nöckler et al., "*Experimental studies in pigs on Trichinella detection in different diagnostic matrices,*" Veterinary Parasitology 132 (2005) 85-90 doi: 10.1016/j.vetpar.2005.05.033.
Notredame et al., "*T-Coffee: A novel method for multiple sequence alignments,*" J. Mol. Biol. (2000) 302, 205-217 doi: 10.1006/jmbi.2000.4042.
PanReac AppliChem ITW Reagents advertisement, 2 pages, obtained Jan. 27, 2020 from internet: https://www.itwreagents.com/download_file/info_point/IP-036/en/IP-036_en.pdf.
Retsch Technology GmbH, "*CAMSIZER® Characteristics—Basis of definition DIN 66141,*" Nov. 5, 2009, 8 pgs.
Takara Bio Complete Digestion of Antibody Types, 4 pages, obtained Jan. 24, 2020 from internet: https://www.takarabio.com/learning-centers/protein-research/mass-spectrometry-digestion-reagents/protein-digestion-with-capturem-pepsin.
Zarlenga et al., "*Identification and classification within the genus, Trichinella, with special emphasis on non-encapsulated species*", Veterinary Parasitology 125 (2004) 69-92, pp. 75-78.

ANTIGEN DETECTION OF TRICHINELLA

CROSS-REFERENCE TO RELATED APPLICATIONS

The present application is a continuation of U.S. application Ser. No. 16/225,007, filed on Dec. 19, 2018, and claims priority to European patent applications EP 17 208 994.8 filed Dec. 20, 2017 and EP 18 199 404.7 filed Oct. 9, 2018, the contents of each of which are hereby incorporated by reference in their entirety.

REFERENCE TO A SEQUENCE LISTING

The instant application contains a Sequence Listing which has been filed electronically in ASCII format and is hereby incorporated by reference in its entirety. Said ASCII copy, created on Apr. 3, 2020, is named 000710USCONT01_SL_ST_25.txt and is 6,827 bytes in size.

BACKGROUND OF THE INVENTION

Field of the Invention

The present invention is directed at a method of detecting *Trichinella* in a tissue extract sample, the use of a detection system according to the invention for detection of *Trichinella*, and a kit comprising (a) a detection carrier comprising a first antibody against one or more antigens of *Trichinella*, and (b) (i) a second antibody against one or more antigens of *Trichinella*, wherein the second antibody is bound to a signal molecule, or (b) (ii) comprises one or more antigens of *Trichinella* bound to a signal molecule, wherein the antigens of (b) (ii) are configured so as to dissolve binding of the antigens of (a) to the first antibody by competitive displacement.

Description of Related Art

*Trichinella spiralis* (*T. spiralis*) is a nematode of the genus *Trichinella* and can cause serious human diseases. So-called trichinellosis is caused by the consumption of raw or insufficiently heated meat, which is infected with *Trichinella*. Symptoms of this disease are initially nausea, diarrhea and muscle pain. As the disease progresses, paralysis, facial swelling—especially periorbital —, conjunctivitis, headache, rash, and myocarditis are added, among other things [1]. Generally, the parasite is transmitted by the meat of various mammals such as domestic pigs, horses, bears, wild boars or rodents. Eleven different species of the genus *Trichinella* are known, which can be divided into two groups: species such as *T. spiralis*, which form a collagen capsule in the muscle cell of the host organism, by which they are permanently encapsulated, and species that do not form a capsule, such as *T. pseudospiralis* [2].

With few exceptions, *T. spiralis* is climate-dependent and occurs worldwide. In the European Union (EU), there are rarely cases of trichinellosis in domestic swine derived from commercial breeding and fattening farms, but the prevalence is clearly higher in the case of wild animals such as wild boars, foxes, and raccoon dogs or privately kept pigs. In China, the prevalence in pigs is generally up to 4%. There, over 500 outbreaks occurred between 1964 and 2002, with a total of over 25,000 sick persons [3].

The life cycle of *T. spiralis* is widely known. After oral ingestion of foods infected with *T. spiralis*, the larvae are released into the small intestine after approximately 24 h, due to the collagen capsule being decomposed by the digestive fluid. Over four molts, the larva develops into an adult form, and fertilization of the females occurs. After 5-10 days, new larvae are born (NBL—New Born Larvae) that spread through the blood and lymphatic system. 6-12 days later, the larvae invade the striated musculature (ML—muscle larvae), and after 4-6 weeks, capsule formation begins, with the capsule increasingly calcifying over time. Over years to decades, a metabolic exchange with the tissue takes place [4].

To survive for years in the host's muscles, *T. spiralis* manipulates the host immune system with the help of numerous proteins that are secreted into the surrounding tissue. The so-called excretory and secretory proteins (E/S proteins) are predominantly secreted by the stichosome, which consists of about 50 large glandular cells, the stichocytes, and is located in the esophageal wall.

*Trichina* examination, formerly called *Trichina* inspection, is an examination of meat from food-producing animals for *T. spiralis* after slaughter. It is part of the official inspection before slaughter and after slaughter of slaughter animals subject to examination, and was introduced because of several epidemics that occurred in the middle of the 19th century. Thus, the obligatory *Trichina* inspection was introduced in the Kingdom of Prussia as early as 1866. If the meat is to be released for human consumption, all animals within the EU which may be carriers of *T. spiralis*, e.g. domestic pigs, horses, bears or wild boars must be examined (EC No. 2015/1375).

The costs of the *Trichina* examination are (0.12 to € 3.70 per pig, depending on the size of the slaughterhouse and the associated amount of slaughtered animals [5].

Serology is not useful in the *Trichina* examination, as seroconversion takes place at an infectious dose of 20,000 larvae after 3-4 weeks and of 100 larvae after 5-7 weeks [6].

There are several detection systems for the detection of *T. spiralis* in tissue, which are permissible according to EU Regulation (EC No. 2015/1375), and are used in slaughterhouses or in the laboratory. In addition to the mechanically assisted method of artificial digestion with the Stomacher Lab-blender 3500, the automatic digestive process for bulk samples up to 35 g with the Trichomatic-35®-Mixer and the test by artificial digestion using the PrioCHECK® *Trichinella* AAD Kit, there are two other methods, namely the magnetic stirring method for artificial digestion of bulk samples, and the "on-filter isolation" technique with larva detection by means of a latex agglutination test (Trichin-L antigen test kit from Bio-Rad). In this context, it should be noted that the most commonly performed method, simultaneously considered to be a reference, is the magnetic stirring method for artificial digestion. The latest method is the magnetic stirring method for artificial digestion of bulk samples with subsequent "on-filter-isolation" technique and larva detection by means of a latex agglutination test.

The magnetic stirring method for artificial digestion of bulk samples is sufficiently known to a person skilled in the art [7]. This method has numerous disadvantages, such as varying quality of the pepsin used, temperature and time sensitivity (digestion should take place for 30 minutes at 46° C. to 48° C.), great time intensity (due to the digestion process, sedimentation steps, equipment cleaning and microscopy), manual evaluation by specially trained personnel, difficult and sometimes dangerous handling of individual steps due to working with hydrochloric acid, for example, difficult evaluation (for example, the digestive fluid may have been washed insufficiently and the larvae may thus be overlooked due to the excessive turbidity), and the risk of contamination due to poorly cleaned equipment.

Also, the "on-filter-isolation" technique and subsequent larva detection by means of the latex agglutination test Trichin-L has numerous disadvantages. For example, the method mentioned here also has the above-mentioned disadvantages in terms of digestion, since the digestion step is identical. Furthermore, the sensitivity of the test can be severely impaired due to chemical products such as detergents in cleaning solutions. In addition, there are many devices that require thorough cleaning, and therefore the risk of contamination is quite high.

Therefore, there is a need for a method which, by being easy to handle, provides fast, inexpensive and above all reliable *Trichinella* detection in animal tissue, especially muscle tissue.

BRIEF SUMMARY OF THE INVENTION

Methods, uses, and kits that allow rapid, inexpensive, and reliable *Trichinella* detection in tissue are described below and are the subject of the described invention.

Embodiments of the present invention include the following:

1. A method of detecting *Trichinella* in a tissue extract sample, wherein 90% of the particles in the tissue extract sample have a diameter of 300 μm or less (D90≤300 μm).
2. The method according to 1, wherein the tissue extract sample is a mammalian sample, preferably a sample from a pig.
3. The method according to one of 1 or 2, wherein 90% of the particles in the tissue extract sample have a diameter of 250 μm or less (D90≤250 μm), preferably 200 μm or less (D90≤200 μm).
4. The method according to one of 1 to 3, wherein the tissue extract sample is from musculature.
5. The method according to one of 1 to 4, wherein in the preparation of the tissue extract sample
(a) a temperature of 45° C., preferably 40° C., is not exceeded; and/or
(b) no enzymatic and/or chemical cleavage of the tissue takes place.
6. The method according to one of 1 to 5, wherein the method
(a) does not comprise a microscopy step;
(b) is used in meat inspection; and/or
(c) has a detection limit of ≤7 ng antigen per ml of tissue extract.
7. The method according to one of 1 to 6, wherein the method is performed by means of an immunoassay, preferably by means of an ELISA, lateral flow assay, line blot assay, Western blot assay, bead-based assay, vertical filtration assay or 3D immunofiltration assay.
8. The method according to one of 1 to 7, wherein *Trichinella* is *Trichinella spiralis.*
9. Use of a detection system for the detection of *Trichinella*, preferably for meat inspection, wherein the detection system
(a) comprises a detection carrier comprising a first antibody against one or more antigens of *Trichinella*, and
(b) (i) comprises a second antibody against one or more antigens of *Trichinella*, wherein the second antibody is bound to a signal molecule, or
(b) (ii) comprises one or more antigens of *Trichinella* bound to a signal molecule, wherein the antigens of (b) (ii) are configured so as to dissolve binding of the antigens of (a) to the first antibody by means of competitive displacement.
10. Kit comprising
(a) a detection carrier comprising a first antibody against one or more antigens of *Trichinella*, and
(b) (i) a second antibody against one or more antigens of *Trichinella*, wherein the second antibody is bound to a signal molecule, or
(b) (ii) comprises one or more antigens of *Trichinella* bound to a signal molecule, wherein the antigens of (b) (ii) are configured so as to dissolve binding of the antigens of (a) to the first antibody by means of competitive displacement.
11. The kit according to 10, wherein the kit further comprises a description of a method according to one of 1 to 8.

DETAILED DESCRIPTION OF THE INVENTION

Figure 1:
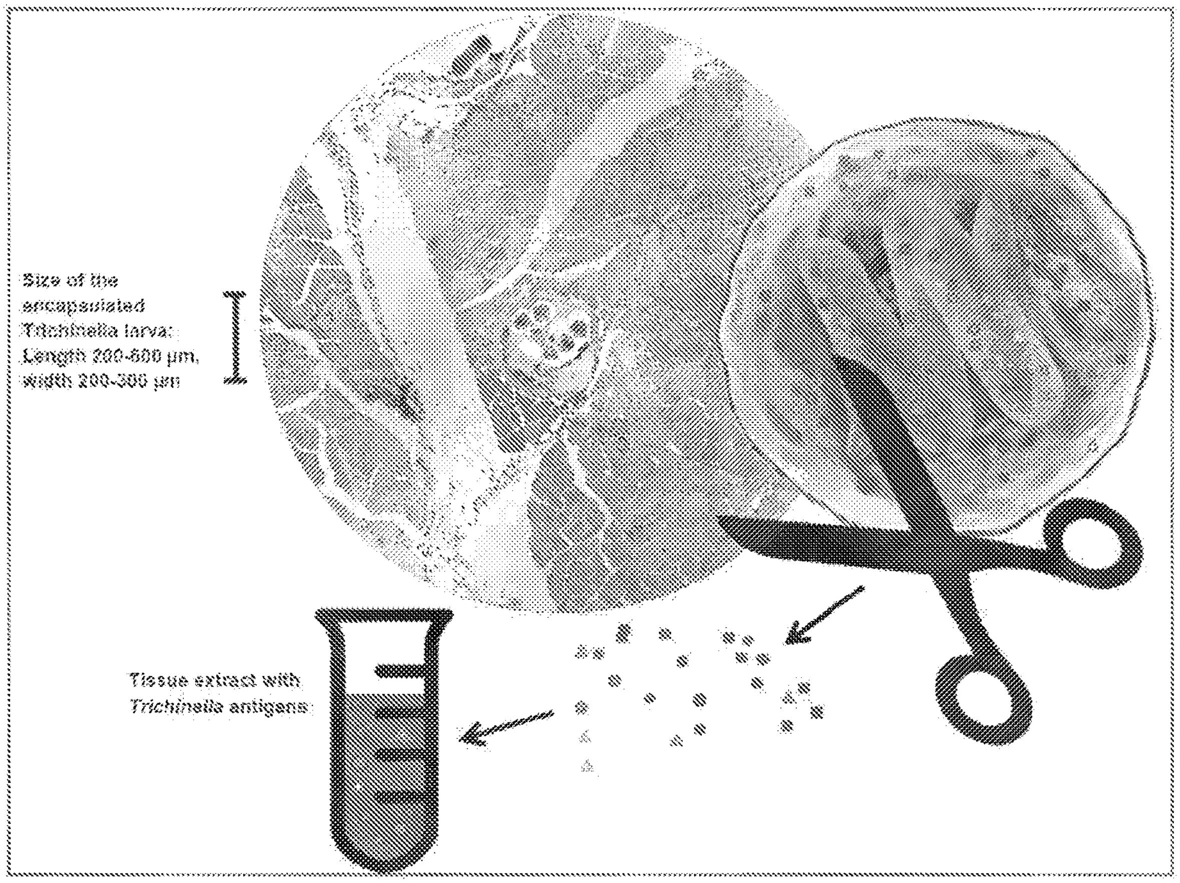
FIG. 1 shows the E/S proteins of an encapsulated *Trichinella spiralis* larva. The E/S proteins are secreted by the larva into the capsule and into the surrounding tissue. By comminuting the tissue, the proteins are released into the sample material.

The inventors of the present invention have surprisingly found that *Trichinella* detection can be achieved by immunoassay by means of (mechanical) comminution of *Trichinella*-infected tissue. Such an assay allows the detection of ≤7 ng *Trichinella* antigen per ml of tissue extract or less. In particular, it was possible to show that as soon as 90% of the particles contained in the tissue extract sample have a diameter of 300 μm or less (D90≤300 μm), efficient detection of *Trichinella* can take place.

In a first aspect, therefore, the present invention is directed at a method of detecting *Trichinella* in a tissue extract sample, wherein 90% of the particles in the tissue extract sample have a diameter of 300 μm or less (D90≤300 μm). *Trichinella* is preferably detected by immunoassay, by detecting an antigen of *Trichinella*, preferably an antigen specific for *Trichinella* in the tissue extract sample.

In preferred embodiments of the invention, the tissue extract sample is a mammalian sample, preferably a sample from a pig.

In preferred embodiments, in the tissue extract sample 90% of the particles have a diameter of 100 μm or less (D90≤100 μm), preferably 20 μm or less (D90≤20 μm).

In other preferred embodiments, the tissue extract sample is derived from musculature.

In preferred embodiments of the method according to the invention, (a) a temperature of 45° C., preferably 40° C., is not exceeded in the preparation of the tissue extract sample and/or (b) there is no enzymatic and/or chemical cleavage of the tissue.

Furthermore, in preferred embodiments (a), the method does not comprise a microscopy step; (b) use in the context of meat inspection and/or (c) has a detection limit of ≤7 ng antigen per ml of tissue extract.

In further preferred embodiments, the method of the invention is performed by means of an immunoassay, more preferably by means of an ELISA, line blot assay, Western blot assay, bead-based assay, lateral flow assay, vertical filtration assay, or 3D immunofiltration assay.

In preferred embodiments, *Trichinella* is *Trichinella spiralis.*

In a second aspect, the present invention is directed at use of a detection system for the detection of *Trichinella*, preferably in the context of meat inspection, wherein the detection system comprises (a) a detection carrier comprising a first antibody against one or more antigens of *Trichinella*, and (b) (i) a second antibody against one or more antigens of *Trichinella*, wherein the second antibody is bound to a signal molecule, or (b) (ii) comprises one or more antigens of *Trichinella* that are bound to a signal molecule, wherein the antigens of (b) (ii) are configured in such a manner that they dissolve binding of the antigens of (a) to the first antibody by competitive displacement.

In a third aspect, the present invention is directed at a kit comprising (a) a detection carrier comprising a first antibody against one or more antigens of *Trichinella*, and (b) (i) a second antibody against one or more antigens of *Trichinella*, wherein the second antibody is bound to a signal molecule, or (b) (ii) comprises one or more antigens of *Trichinella* bound to a signal molecule, wherein the antigens of (b) (ii) are configured so as to dissolve binding of the antigens from (a) to the first antibody by competitive displacement.

In a preferred embodiment, the kit further includes a description of a method according to the invention for detecting *Trichinella.*

As already described, the first aspect of the present invention is directed at a method of detecting *Trichinella* in a tissue extract sample, wherein 90% of the particles in the tissue extract sample have a diameter of 300 μm or less (D90≤300 μm).

The term "detection" or "detecting" as used equivalently herein describes the qualitative or quantitative determination of *Trichinella*. Qualitative determination means that only the presence or absence of *Trichinella* is determined. Quantitative determination refers to determination of the relative or absolute amount of *Trichinella* in a sample.

The term "*Trichinella*" or "trichinae" as used equivalently herein refers to a genus of nematode worms (strain Nematoda) with a parasitic lifestyle. Mammals, and therefore humans, and birds serve as intermediate and final hosts. The main carriers to humans are infected pigs or their raw meat, for example consumed as ground pork, or insufficiently cooked meat. Taxonomically, trichinae are classified as follows: Strain: nematodes (Nematoda); Class: Adenophorea (Adenophorea); Subclass: Enoplea (Enoplea); Order: Trichocephalida; Family: Trichinellidae; Genus: *Trichinella*. In preferred embodiments of the invention, *Trichinella* is selected from the group consisting of *Trichinella spiralis, Trichinella nativa, Trichinella britovi, Trichinella murrelli, Trichinella* T6, *Trichinella* T7, *Trichinella nelsoni, Trichinella* T8, *Trichinella* T9, *Trichinella pseudospiralis, Trichinella papuae*, and *Trichinella zimbabwensis*. In further preferred embodiments, the *Trichinella* species is an organism that forms a collagen capsule in a muscle cell of the host organism and is permanently encapsulated by it. In a still further preferred embodiment, *Trichinella* is *Trichinella spiralis. Trichinella spiralis* is a nematode and, in Central Europe, the most important representative of trichinae. It occurs worldwide, but it does not have much significance in tropical regions. *T. spiralis* causes the clinical picture of trichinellosis.

The term "tissue extract sample" as used herein refers to a mixture of various substances of biological origin. The material of biological origin may be epithelial tissue (cell layers covering all internal and external surfaces), connective and supporting tissue (tissue that provides structural cohesion and fills spaces), specialized tissue (such as blood, free cells, etc.), muscle tissue (cells that are specialized for active movement by contractile filaments), nerve tissue (cells that make up the brain, spinal cord, and peripheral nerves), and tissue fluid, such as the lymph system. More preferably, the tissue is muscle tissue. The muscle tissue may be smooth musculature, cardiac musculature and/or skeletal musculature. In further preferred embodiments, the sample is taken from the diaphragm, tongue or intercostal muscles of the subject to be examined. Preferably, the tissue is a solid tissue.

A tissue extract sample can be either heterogeneous or homogeneous. A heterogeneous tissue extract sample includes tissues of various tissue types. A homogeneous tissue extract sample comprises only a given tissue. A homogeneous tissue extract sample is preferred. In alternative embodiments, the sample is a pooled sample, i.e. the sample material comes from different individuals. Or the sample comes exclusively from a single individual.

The extract can be obtained from pieces of tissue or viable cells. These are comminuted and mixed with an aqueous solution, such as buffer solutions, $H_2O$, cell media and mixtures thereof. Preferably, the manufacturing process does not involve cell cultivation.

In preferred embodiments of the invention, the tissue extract sample is a mammalian sample. In further preferred embodiments, the sample is from pigs, horses, bears, cats, dogs, rodents or humans. Even more preferably, the sample comes from a domestic pig (*Sus scrofa domesticus*), a wild boar (*Sus scrofa*), Pomeranian pig (*Sus salvanius*), bearded pig (*Sus barbatus*), Palawan bearded pig (*Sus ahoenobarbus*), Annamite pustule pig (*Sus bucculentus*), Visayas pustule pig (*Sus cebifrons*), Sulawesi pustule pig (*Sus celebensis*), Mindoro pustule pig (*Sus oliveri*), Philippine pustule pig (*Sus philippensis*), Javanese pustule pig (*Sus verrucosus*) or Bawean pustule pig (*Sus blouchi*).

The term "particle diameter" as used herein refers to a volumetric or length measurement of the particles being examined in the tissue extract. The particles studied may have a roughly roundish shape or an elongated fibrous structure. In preferred embodiments, 90% of the particles in the tissue extract sample have a diameter of 300 μm or less (D90≤300 μm), 290 μm or less (D90≤290 μm), 280 μm or less (D90≤280 μm), 270 μm or less (D90≤270 μm), 260 μm or less (D90≤260 μm), 250 μm or less (D90≤250 μm), 240 μm or less (D90≤240 μm), 230 μm or less (D90≤230 μm), 220 μm or less (D90≤220 μm), 210 μm or less (D90≤210 μm), 200 μm or less (D90≤200 μm), 190 μm or less (D90≤190 μm), 180 μm or less (D90≤180 μm), 170 μm or less (D90≤170 μm), 160 μm or less (D90≤160 μm), 150 μm or less (D90≤150 μm), 140 μm or less (D90≤140 μm), 130 μm or less (D90≤130 μm), 120 μm or less (D90≤120 μm), 110 μm or less (D90≤≤110 μm), 100 μm or less (D90≤100 μm), 95 μm or less (D90≤95 μm), 90 μm or less (D90≤90 μm), 85 μm or less (D90≤85 μm), 80 μm or less (D90≤80 μm), 75 μm or less (D90≤75 μm), 70 μm or less (D90≤70 μm), 65 μm or less (D90≤65 μm), 60 μm or less (D90≤60 μm), 55 μm or less (D90≤55 μm), 50 μm or less (D90≤50 μm), 45 μm or less (D90≤45 μm), 40 μm or less (D90≤40 μm), 35 μm or less (D90≤35 μm), 30 μm or less (D90≤30 μm), 25 μm or less (D90≤25 μm), 20 μm or less (D90≤20 μm), 17 μm or less (D90≤17 μm), 15 μm or less (D90≤15 μm), 13 μm or less (D90≤13 μm), 10 μm or less (D90≤10 μm), 8 μm or less (D90≤8 μm) or 6 μm or less (D90≤6 μm).

The particle diameter measurement may take place by devices using dynamic image analysis (e.g., Camsizer® XT from Retsch) or devices based on the principle of static laser scattering (e.g., LA-960 from HORIBA). The particle size can be measured in $x_{c\ min}$ and is defined in accordance with DIN 66141 as follows: Shortest particle diameter of the measurements of the maximum diameters within a particle projection (English: particle diameter which is the shortest chord of the measured set of maximum chords of a particle projection) [10]. Alternatively, the particle size can be measured using the Feret diameter ($x_{Fe}$). The Feret diameter is a measure of the object size along a particular direction. In general, it can be defined as the distance between the two parallel planes that constrain the object perpendicular to that direction. It is therefore also called the caliber diameter, based on the measurement of the object size with a caliper. When analyzing particle sizes, for example in microscopy, where the Feret diameter is applied to projections of a three-dimensional (3D) object on a 2D plane, this is defined as the distance between two parallel tangential lines instead of two planes. For a convex particle, the mean Feret diameter (mean of all directions) is equal to the diameter of a circle of equal circumference. The maximum Feret diameter is the longest Feret diameter within the measured set of Feret diameters. The minimum Feret diameter is the shortest Feret diameter within the measured set of Feret diameters.

Alternatively, the diameter refers to an average diameter, wherein the sum of the diameter measurements of all measured measurable particles is divided by the total number of particles measured. In another alternative embodiment, the diameter, when used in relation to the size of the particles, may refer to "D50" such that about 50% of all particles measured have a particle diameter smaller than the defined mean particle diameter value, and that about 50% of all measurable particles measured have a particle diameter larger than the defined mean particle diameter value.

In preferred embodiments of the method according to the invention, in the preparation of the tissue extract sample (a) a temperature of 100° C., 90° C., 80° C., 70° C., 60° C., 55° C., 50° C., 45° C., 44° C., 43° C., 42° C., 41° C., 40° C., 39° C. or 38° C. and/or (b) there is no enzymatic and/or chemical cleavage of the tissue.

The term "preparation of the tissue extract sample" as used herein refers to a multi-step process wherein a tissue sample is taken from an organism to be examined, this tissue sample (mechanically) minced, and the minced tissue sample treated by filtration and/or centrifugation. Subsequently, the antigen detection can be carried out in the process according to the invention.

The comminution of the tissue sample is preferably carried out purely mechanically, i.e., for example, no enzymatic and/or chemical cleavage of the tissue. Mechanical comminution can take place by cutting, ripping or crushing, but is preferably achieved by cutting (for example via a knife mill). By comminution of the tissue sample, *Trichinella* larvae also located in the tissue sample are comminuted. The comminuted *Trichinella* larvae have a size corresponding to the comminuted tissue after comminution.

In a preferred embodiment, the term "no enzymatic cleavage" as used herein refers to the fact that no enzymes are used to comminute the tissue sample. In particular, no proteases (e.g., pepsin), lipases, amylases, cutinases, cellulases, or hemicellulases are used to comminute the tissue sample.

In a preferred embodiment, the term "no chemical cleavage" as used herein refers to the fact that no chemical substances such as acids, bases, oxidants, etc. are used to comminute the tissue sample.

Furthermore, in preferred embodiments (a), the method does not comprise a microscopy step; (b) use in meat inspection and/or (c) has a detection limit of <20 ng, <15 ng, <10 ng, <9 ng, <8 ng, <7 ng, <6 ng, <5 ng, <4 ng, <3 ng, <2 ng, <1 ng, <0.5 ng, <0.25 ng, <0.1 ng, <0.05 ng, <0.01 ng, <0.005 ng or <0.001 ng of antigen per ml of tissue extract.

The term "no microscopy step" as used herein refers to the evaluation of a method for *Trichinella* detection, wherein no microscope or microscopic evaluation, in particular a manual microscopic evaluation, is necessary for the evaluation of the method according to the invention.

The term "meat inspection" or "inspection before slaughter and after slaughter," as used herein, refers to a process intended to ensure that the meat of certain species of animals is put into commerce as food only if it is considered fit for consumption by humans. This investigation is an integral part of measures to ensure meat hygiene. The examination is usually carried out by official veterinarians or meat inspectors in two stages, namely the examination of the animal and the examination of the meat.

In a preferred embodiment, the term "detection limit" as used herein indicates the least amount of a substance (antigen) that can be distinguished from the absence of that substance with a specific probability. Alternatively, the term "detection limit" may refer to the concentration of an antigen in a solution, where the measured value is greater than the associated uncertainty. The detection limit can be arbitrarily defined as 3 standard deviations (SD) away from the zero concentration.

In further preferred embodiments, the method of the invention is performed by means of an immunoassay, more preferably by an ELISA, line blot assay, Western blot assay, bead-based assay, lateral flow assay, vertical filtration assay, or 3D immunofiltration assay.

In a preferred embodiment, the term "immunoassay" as used herein refers to the detection or quantification of an analyte—such as a given antigen of *Trichinella*—comprising an immune reaction between an antibody and the antigen. In the context of the invention, the analyte to be detected or quantified may comprise a peptide, a post-translationally modified peptide, preferably a glycoprotein, a sugar, a lipid, a nucleic acid and/or another molecule of *Trichinella*.

In a preferred embodiment, the term "ELISA" as used herein stands for Enzyme-linked Immunosorbent Assay and refers to an antibody-based detection method (assay). The ELISA belongs to the group of immunoassay methods based on an enzymatic color reaction and thus belongs to the enzymatic immunoadsorption methods (EIA). Preferred embodiments include direct ELISA, indirect ELISA, direct sandwich ELISA, bridging ELISA, indirect sandwich ELISA, and competitive ELISA. A person skilled in the art is familiar with the stated form and other forms and derivatives of ELISA.

In a preferred embodiment, the term "lateral flow assay" as used herein (English for "lateral flow test") is a biochemical method for the qualitative detection of materials/substances/antigens with antibodies. The lateral flow assay is a combination of thin layer chromatography and immunostaining. The lateral flow assay can be used in the form of a test strip.

In a preferred embodiment, the term "vertical filtration assay" as used herein is based on contacting ligands/antigens to be tested with a membrane on which captor antibodies are immobilized. This is followed by a washing process to remove weakly bound molecules and detection of bound ligands. The difference between lateral flow assay and vertical filtration assay is the lateral and vertical flow of the test fluid. Vertical flow technology has several advantages over the lateral flow assay, for example shorter assay times may occur.

In a preferred embodiment, the term "3D immunofiltration assay" as used herein refers to an immunological rapid assay in flow-through assay format based on the same biochemical principle of analyte recognition by receptor structures as the lateral flow assay. The difference is that the addition of the sample/antigen, conjugate and additional wash solutions occurs sequentially on a three-dimensional porous shaped body on which captor antibodies are immobilized. All solutions and their constituents, such as analytes/antigens and detection reagents, flow into the depth of the shaped body by means of through-flow. By utilizing enrichment effects, it is possible to increase detection limits.

In a preferred embodiment, the term "line blot" refers to a test strip to which at least one purified antigen is applied by printing on a precisely predetermined position on the strip. The preparation of such test strips is described in the prior art. If antibodies are present in the sample, its complex can be detected colorimetrically with the antigen. The reading is done visually or by intensity measurement of resulting bands. The test strip may contain a positive control in the form of a band that appears when the strip has been incubated with serum, irrespective of whether or not it contains the analyte to be detected.

In a preferred embodiment, the term "bead-based assay" refers to a test in which the carrier used is a bead, preferably a magnetic bead, on which a reagent for the detection, preferably an antibody against an antigen of *Trichinella*, is immobilized. Detection of the antibody-antigen complex can be carried out by chemiluminescence, preferably by means of a second antibody which carries a signal molecule detectable by chemiluminescence. The bead is preferably chemically inert and comprises slow-reacting carbohydrates.

In preferred embodiments of the method according to the invention, this method comprises the following steps:

(a) providing a detection carrier comprising a first antibody against one or more antigens of *Trichinella;*

(b) contacting the detection carrier with the sample;

(c) (i) contacting the detection carrier and any sample material bound thereto with a second antibody against one or more antigens of *Trichinella*, wherein the second antibody is bound to a signal molecule and wherein the presence of a signal of the signal molecule indicates the presence of *Trichinella* in the sample; or (c) (ii) contacting the detection carrier and, if applicable, any sample material bound thereto with one or more antigens of *Trichinella*, wherein the antigens of (c) (ii) are bound to a signal molecule and configured so as to dissolve binding of the antigens from (a) to the first antibody by competitive displacement, wherein the presence of a signal of the signal molecule indicates the presence of *Trichinella* in the sample.

In further preferred embodiments, in each case a washing step takes place after the contacting steps (b), (c) (i) and (c) (ii).

Furthermore, in preferred embodiments of the method, of use and of the kit, the signal molecule can be observed using analytical techniques such as fluorescence measurement, chemiluminescence measurement, radioactivity measurement, electron spin resonance measurement, ultraviolet/visible absorption spectroscopy, mass spectrometry, nuclear magnetic resonance, magnetic resonance and electrochemical measurement methods.

Suitable antigens of *Trichinella* are known from the state of the art. Preferably, the antigen is tyvelose.

In preferred embodiments, the first and second antibodies are directed against different epitopes of the same antigen.

In further preferred embodiments, the first and/or second antibody is selected from the group consisting of an antibody which is directed against a post-translational modification (possibly bound to a substrate protein), preferably a molecule comprising tyvelose, an antibody which is directed against an excretory-secretory (E/S) antigen of *Trichinella*, and an antibody prepared using a lysate of *Trichinella spiralis*.

The term "antibody" as used herein refers to proteins from the class of globulins that are formed in vertebrates in response to certain substances called antigens. Antibodies are components of the immune system. Antibodies are produced by a class of white blood cells called B lymphocytes. They can be differentiated using different classes, namely immunoglobulin A, immunoglobulin D, immunoglobulin E, immunoglobulin G, immunoglobulin M, immunoglobulin W, and immunoglobulin Y. In preferred embodiments, the first and/or the second antibody is/are immunoglobulin G.

In preferred embodiments, the antibodies used are selected from the group consisting of an antibody comprising a VH sequence according to SEQ ID NO: 1 and a VL sequence according to SEQ ID NO: 2, an antibody comprising a VH sequence according to SEQ ID NO: 3 and a VL sequence according to SEQ ID NO: 4, antibody 18H1 (IgG2a), which binds tyvelose and is described in [11], and variants of these.

The term "variant" as used herein refers to antibodies and VH and VL sequences that possess at least 70%, at least 75%, at least 80%, at least 85%, at least 90%, at least 95%, at least 97%, or at least 99% homology with the reference antibody or with the reference sequence. Preferably, only those variants are used which have biological activity. "Biological activity" as used in this context means, in particular, that the corresponding peptides have at least 30%, at least 40%, at least 50%, at least 60%, at least 70%, at least 80%, at least 90%, at least 95% of the specific binding activity of their reference antibody or of the reference sequence. Functional fragments or derivatives of antibodies or variants thereof, for example Fab, F (ab'), Fr, ScTv and dAb or aptamers with corresponding binding activity, can be used.

In a preferred embodiment of the method according to the invention, comminution of the tissue extract sample is carried out exclusively mechanically. In other words, in this embodiment there is no comminution step that is carried out chemically and/or enzymatically by molecules or compounds externally added to the process. In other preferred embodiments, no additional external chemical and/or enzymatic molecules are added to the method in an amount such that the proteolytic activity achieves more than four times, more than three times or more than twice the background proteolytic activity.

In a further preferred embodiment of the process according to the invention, at least 30%, at least 35%, at least 40%, at least 45%, at least 50%, at least 55%, at least 60%, at least 65%, at least 70%, at least 75%, at least 80%, at least 85%, at least 90%, at least 95%, at least 97% or at least 99% of all protease cleavage sites are not cleaved in the tissue extract sample. These proteases possess a hydrolytic activity with regard to peptide bonds and belong to EC class 3.4.

In other preferred embodiments of the process according to the invention, at least 30%, at least 35%, at least 40%, at least 45%, at least 50%, at least 55%, at least 60%, at least 65%, at least 70%, at least 75%, at least 80%, at least 85%, at least 90%, at least 95%, at least 97% or at least 99% cleavage sites of pepsin, chymosin, cathepsin E, papain, cathepsin K, caspase, calpain, scytalidoglutamic peptidase, thermolysin, collagenases, carboxypeptidase A and B, chymotrypsin, plasmin, thrombin, trypsin, granzymes and/or kallikrein are not cleaved in the tissue extract sample.

In a further preferred embodiment of the process according to the invention, at least 30%, at least 35%, at least 40%, at least 45%, at least 50%, at least 55%, at least 60%, at least 65%, at least 70%, at least 75%, at least 80%, at least 85%, at least 90%, at least 95%, at least 97% or at least 99% cleavage sites of pepsin, chymosin, chymotrypsin and/or trypsin are not cleaved in the tissue extract sample. In particular, in the tissue extract sample, at least 30%, at least 35%, at least 40%, at least 45%, at least 50%, at least 55%, at least 60%, at least 65%, at least 70%, at least 75%, at least 80%, at least 85%, at least 90%, at least 95%, at least 97% or at least 99% cleavage sites of pepsin are not cleaved.

The cleavage sites of the above peptidases are sufficiently known from the state of the art, for example https://web-.expasy.org/peptide_cutter/peptidecutter_enzymes.html#Peps, and are hereby incorporated in the description by reference.

The identity/homology of nucleic acid or amino acid sequences is determined by sequence comparison. This sequence comparison is based on the BLAST algorithm established in the prior art and commonly used (compare [12] and [13]) and is principally achieved by assigning similar sequences of nucleotides or amino acids in the nucleic acid or amino acid sequences to one another. A tabular assignment of the relevant positions is referred to as alignment. Another algorithm available in the prior art is the FASTA algorithm. Sequence comparisons (alignments), in particular multiple sequence comparisons, are created with computer programs. Frequently used, for example, are the Clustal series (see, for example, [14]), T-Coffee (see, for example, [15]) or programs based on these programs or algorithms. Furthermore, sequence comparisons (alignments) are possible using the computer program Vector NTI® Suite 10.3 (Invitrogen Corporation, 1600 Faraday Avenue, Carlsbad, Calif., USA) with the predetermined default parameters; the AlignX module of this program for sequence comparisons is based on ClustalW.

Such a comparison also allows a statement about the similarity of the compared sequences to each other. It is usually given in percent identity, that is, the proportion of identical nucleotides or amino acid radicals at the same position or in positions corresponding to one another in an alignment. The broader term of homology takes preserved amino acid substitutions in amino acid sequences into consideration, in other words amino acids with similar chemical activity, since these usually perform similar chemical activities within the protein. Therefore, the similarity of the sequences compared may also be stated as percent homology or percent similarity. Identity and/or homology information can be made about whole polypeptides or genes or only about individual regions. Homologous or identical regions of different nucleic acid or amino acid sequences are therefore defined by matches in the sequences. Such areas often have identical functions. They can be small and comprise only a few nucleotides or amino acids. Often, such small regions perform essential functions for the overall activity of the protein. It may therefore be useful to relate sequence matches only to individual, possibly small areas. Unless otherwise indicated, however, identity or homology information in the present application refers to the total length of the nucleic acid or amino acid sequence indicated.

The phrase "configured so as to dissolve binding of the antigens to the antibody by competitive displacement," as used herein, refers to antigens that compete with already bound antigens for binding to a given antibody. The competitive antigens are structurally similar to each other and therefore the antigens can be referred to as structural analogs. The displacing antigen may have a higher affinity for the antibody than the displaced antigen and/or the displacing antigen is present in higher concentration than the displaced antigen.

The term "antigen" as used herein preferably refers to substances to which antibodies and certain lymphocyte receptors can specifically bind. Antigens can be proteins, but also glycoproteins, carbohydrates, lipids or other substances. In the present case, the antigens are preferably proteins or post-translationally modified proteins.

In a second aspect, the present invention is directed at use of a detection system for the detection of *Trichinella*, preferably for meat inspection, wherein the detection system comprises (a) a detection carrier comprising a first antibody against one or more antigens of *Trichinella*, and (b) (i) a second antibody against one or more antigens of *Trichinella*, wherein the second antibody is bound to a signal molecule, or (b) (ii) comprises one or more antigens of *Trichinella* bound to a signal molecule, wherein the antigens from (b) (ii) are configured so as to dissolve binding of the antigens of (a) to the first antibody by competitive displacement.

The term "detection system" as used herein preferably comprises (a) a detection carrier as defined herein and (b) an antigen or antibody bound to a signal molecule. The components of (a) and (b) act synergistically in such a way that addition of an antigen to be examined results in a binding complex of all the molecules involved, which allows detection of the antigen to be investigated in a sample by way of the presence of a signal.

The term "detection carrier" as used herein preferably refers to a substance to which an antibody against one or more antigens of *Trichinella* is bound. The carrier can be a solid article such as a slide, a 6-well, 12-well, 96-well or 384-well plate, a membrane, preferably a nitrocellulose membrane, a filter material, a bead, preferably a magnetic bead, or a thin-layer chromatography material. Alternatively, the detection carrier may also be a bead, the diameter of such a bead preferably being smaller than 1000 μm, 800 μm, 600 μm, 400 μm, 200 μm, 100 μm, 90 μm, 80 μm, 70 μm, 60 μm, 50 μm, 40 μm, 30 μm, 20 μm, 10 μm or 5 μm. The detection carrier can preferably comprise plastic, glass, metal or a combination thereof.

In a third aspect, the present invention is directed at a kit comprising (a) a detection carrier comprising a first antibody against one or more antigens of *Trichinella*, and (b) (i) a second antibody against one or more antigens of *Trichinella*, wherein the second antibody is bound to a signal molecule, or (b) (ii) comprises one or more antigens of *Trichinella* bound to a signal molecule, wherein the antigens of (b) (ii) are configured so as to dissolve binding of the antigens from (a) to the first antibody by competitive displacement.

The term "kit" as used herein preferably refers to a package provided with containers (e.g. bottles, plates, tubes, cups, etc.), each containing a specific material, in the present case especially a detection carrier as defined herein, and an antigen or antibody bound to a signal molecule. Preferably, the kit is accompanied by instructions for use of the aforementioned material. The instruction manual may be written or printed on paper or another medium, or may be provided in the form of electronic media such as magnetic tape, a computer-readable disk or tape, or CD-ROM. The kit preferably contains a positive control, preferably with an antigen to be detected and/or samples for calibration or creation of a calibration curve.

In a preferred embodiment, the kit furthermore comprises a description of a method according to the invention for detecting *Trichinella.*

FIG. 1 shows the E/S proteins of an encapsulated *Trichinella spiralis* larva. The E/S proteins are secreted by the larva into the capsule and into the surrounding tissue. By comminuting the tissue, the proteins are released into the sample material.

Figure 2:
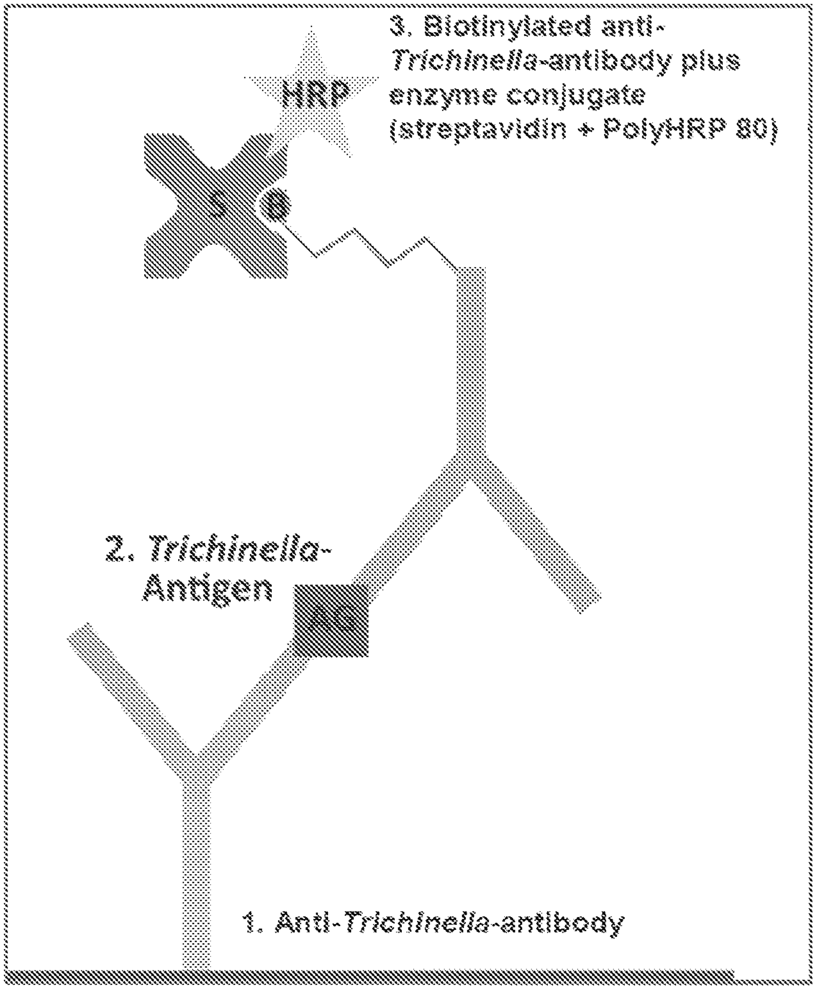
FIG. 2 shows an incubation schematic of the *Trichinella* antigen capture ELISA. 1) Anti-*Trichinella* Ab C9 immobilized on a microtiter plate, 2) sample (*Trichinella* antigen), 3) Biotinylated detection Ab B7 bound to streptavidin with PolyHRP80.

FIG. 2 shows an incubation schematic of the *Trichinella* antigen capture ELISA. 1) Anti-*Trichinella* Ab C9 immobilized on a microtiter plate, 2) sample (*Trichinella* antigen), 3) Biotinylated detection Ab B7 bound to streptavidin with PolyHRP80.

Figure 3:
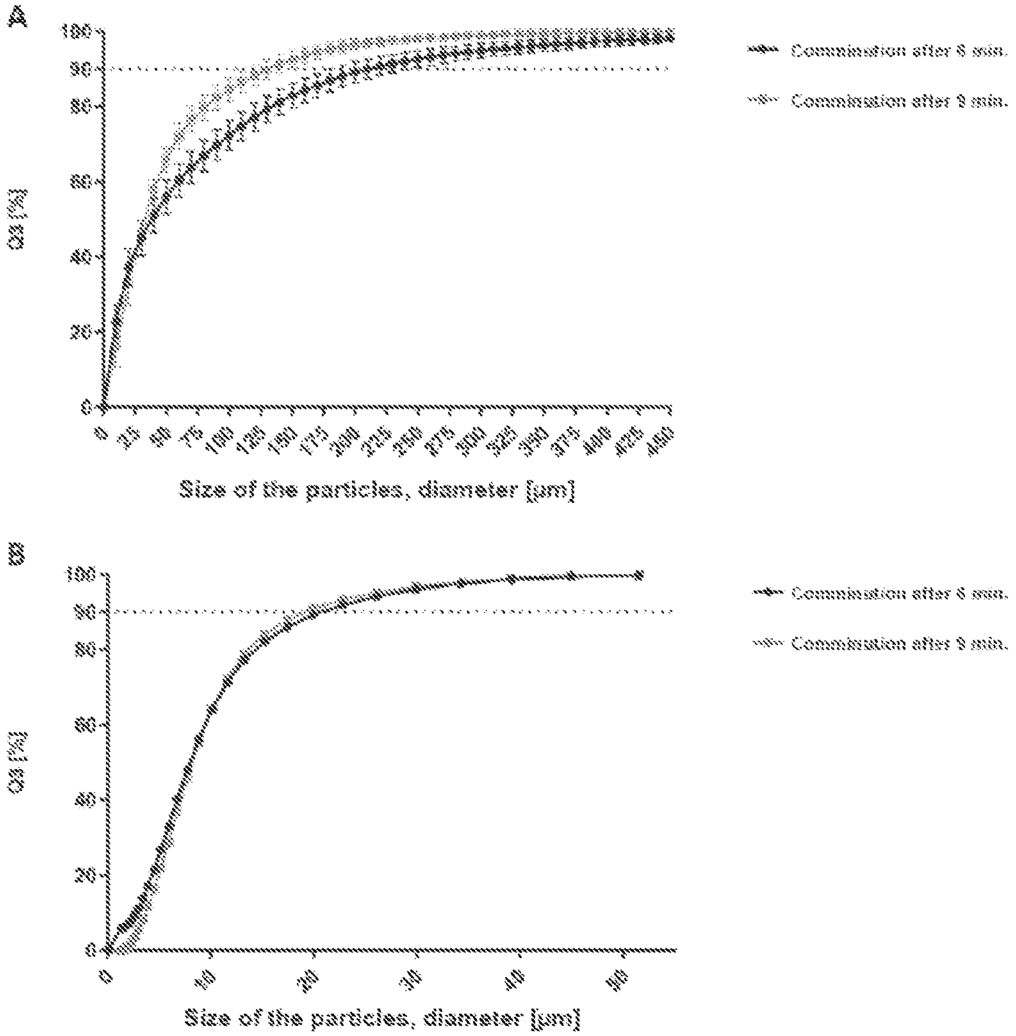
FIG. 3 shows the particle size determination of pork shredded using the GM200 knife mill from Retsch. 100×1 g of diaphragm muscle were comminuted with 200 ml of PBS in the GM200 at 10,000 rpm for 6 and 9 min, respectively. The particle size is plotted against Q3 [%] (volume percent). In each case, about 60 million particles were measured. A) Particle size determination using the Camsizer®XT. n=0.3 B) Particle size determination using the HORIBA LA-960. n=1.

FIG. 3 shows the particle size determination of pork shredded using the GM200 knife mill from Retsch. 100×1 g of diaphragm muscle were comminuted with 200 ml of PBS in the GM200 at 10,000 rpm for 6 and 9 min, respectively. The particle size is plotted against Q3 [%] (volume percent). In each case, about 60 million particles were measured. A) Particle size determination using the Camsizer®XT. n=0.3 B) Particle size determination using the HORIBA LA-960. n=1.

Figure 4:
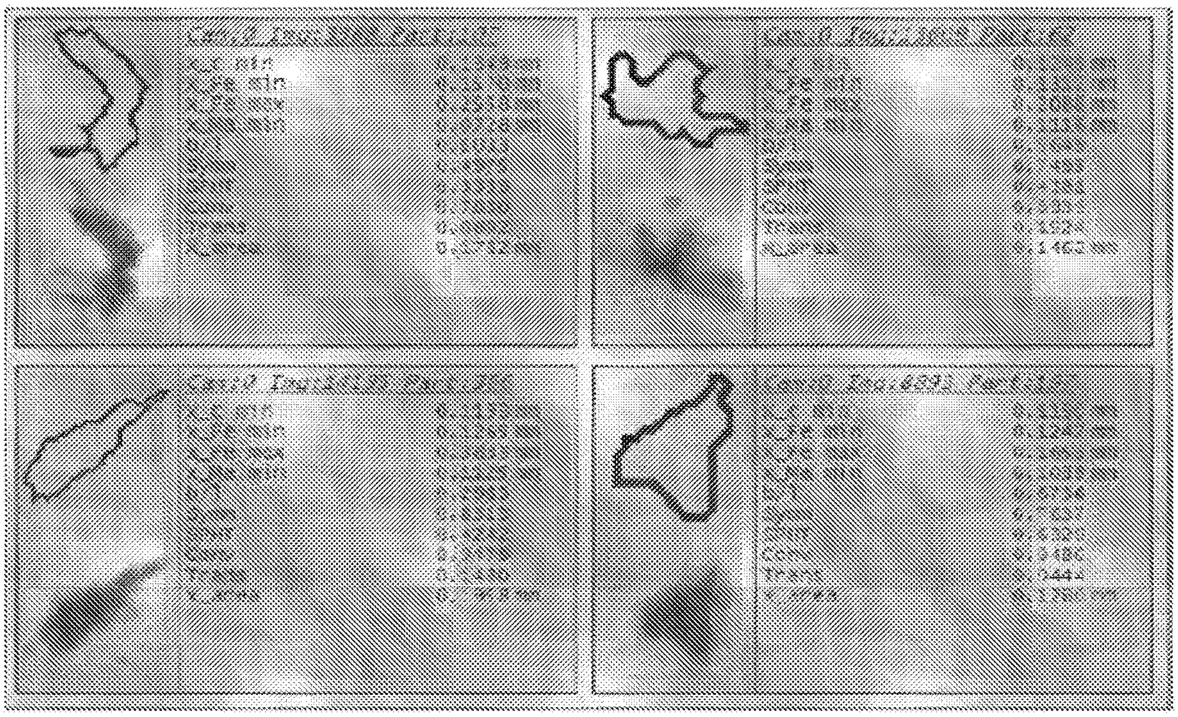
FIG. 4 shows a recorded image of individual meat particles during the measurement using the Camsizer® XT. The shape is generally not round, but rather very fibrous and elongated, so that the width to length ratio decreases.

FIG. 4 shows a recorded image of individual meat particles during the measurement using the Camsizer®XT. The shape is generally not round, but rather very fibrous and elongated, so that the width to length ratio decreases.

Figure 5:
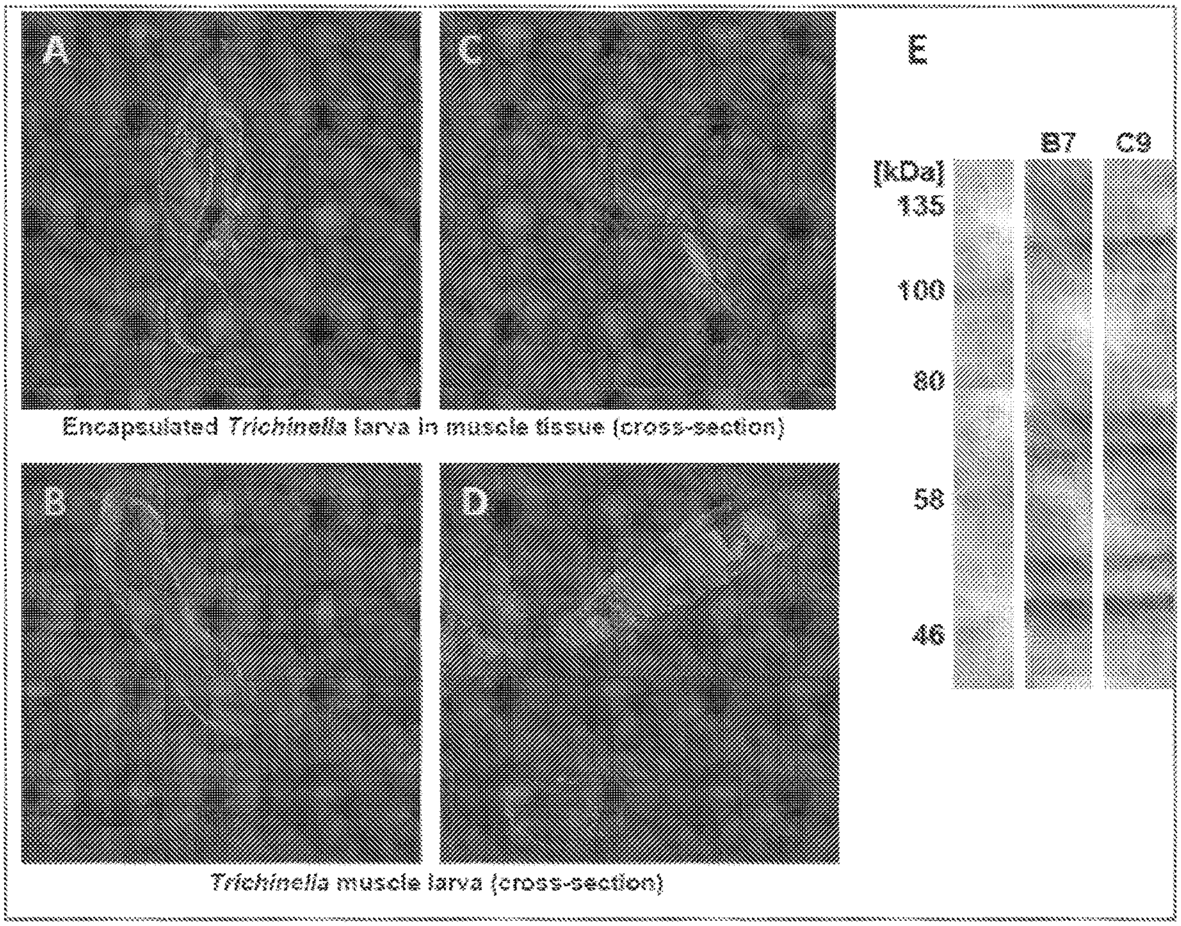
FIG. 5 shows the test of the antibodies anti-[TRISP][B7] and anti-[TRISP][C9] for the detection of *Trichinella*. A)-D) *T. spiralis* IIFT (Indirect Immunofluorescence Test): Ab B7 and Ab C9 were incubated at a concentration of 2 μg/ml. A)+B) Incubation with Ab B7: The Ab shows a clear reaction both in the case of the encapsulated *Trichinella* larva in cross-section and in the case of the muscle larva; C)+D) Incubation with Ab C9: Like B7, the Ab shows a clear reaction both in the case of the encapsulated *Trichinella* larva in cross section and in the case of the muscle larva; E) Western blot: 5 μg of *T. spiralis* lysate are applied in each case, and the incubation was carried out with the Ab B7 and the Ab C9 (concentration 0.4 μg/ml).

FIG. 5 shows the test of the antibodies anti-[TRISP][B7] and anti-[TRISP][C9] for the detection of *Trichinella*. A)-D) *T. spiralis* IIFT (Indirect Immunofluorescence Test): Ab B7 and Ab C9 were incubated at a concentration of 2 μg/ml. A)+B) Incubation with Ab B7: The Ab shows a clear reaction both in the case of the encapsulated *Trichinella* larva in cross-section and in the case of the muscle larva; C)+D) Incubation with Ab C9: Like B7, the Ab shows a clear reaction both in the case of the encapsulated *Trichinella* larva in cross section and in the case of the muscle larva; E) Western blot: 5 μg of *T. spiralis* lysate are applied in each case, and the incubation was carried out with the Ab B7 and the Ab C9 (concentration 0.4 μg/ml).

Figure 6:
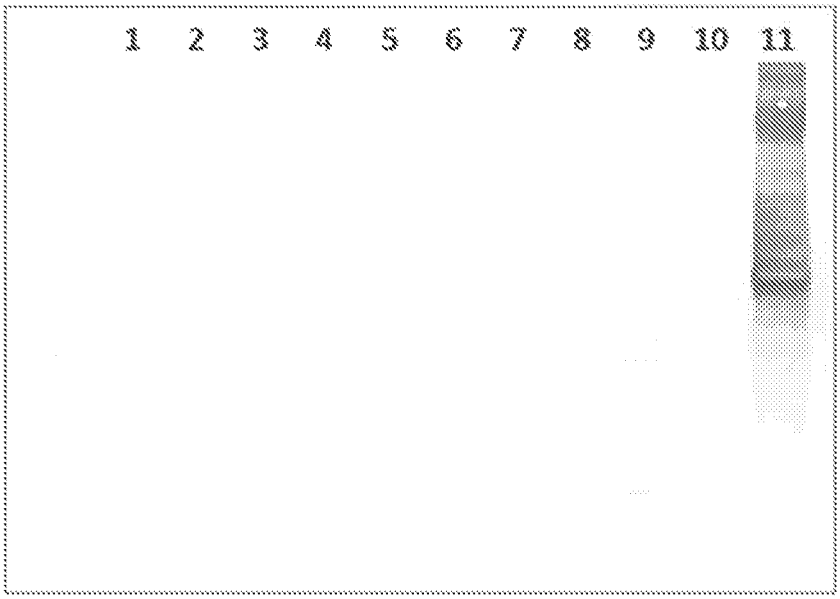
FIG. 6 shows the test of the specificity of the antibodies anti-TRISP[B7] and anti-TRISP[C9] by means of Western blot. Track 1) *Trypanosoma cruzi,* 2) *Ascaris suum,* 3) *Strongyloides ratti,* 4) *Toxocara cati,* 5) *Toxoplasma gondii,* 6) *Salmonella typhimurium,* 7) *Salmonella cholerasuis* strain A, 8) *Salmonella cholerasuis* strain B, 9) *Salmonella typhisuis,* 10) *Trichuris suis,* 11) *Trichinella spiralis*. Applied: 5 μg lysate each. Incubation with Ab B7 (concentration 0.4 μg/ml, 2 h).

FIG. 6 shows the test of the specificity of the antibodies anti-TRISP[B7] and anti-TRISP[C9] by means of Western blot. Track 1) *Trypanosoma cruzi,* 2) *Ascaris suum,* 3) *Strongyloides ratti,* 4) *Toxocara cati,* 5) *Toxoplasmo gondii,* 6) *Salmonella typhimurium,* 7) *Salmonella cholerasuis* strain A, 8) *Salmonella cholerasuis* strain B, 9) *Salmonella typhisuis,* 10) *Trichuris suis,* 11) *Trichinella spiralis*. Applied: 5 μg lysate each. Incubation with Ab B7 (concentration 0.4 μg/ml, 2 h).

Figure 7:
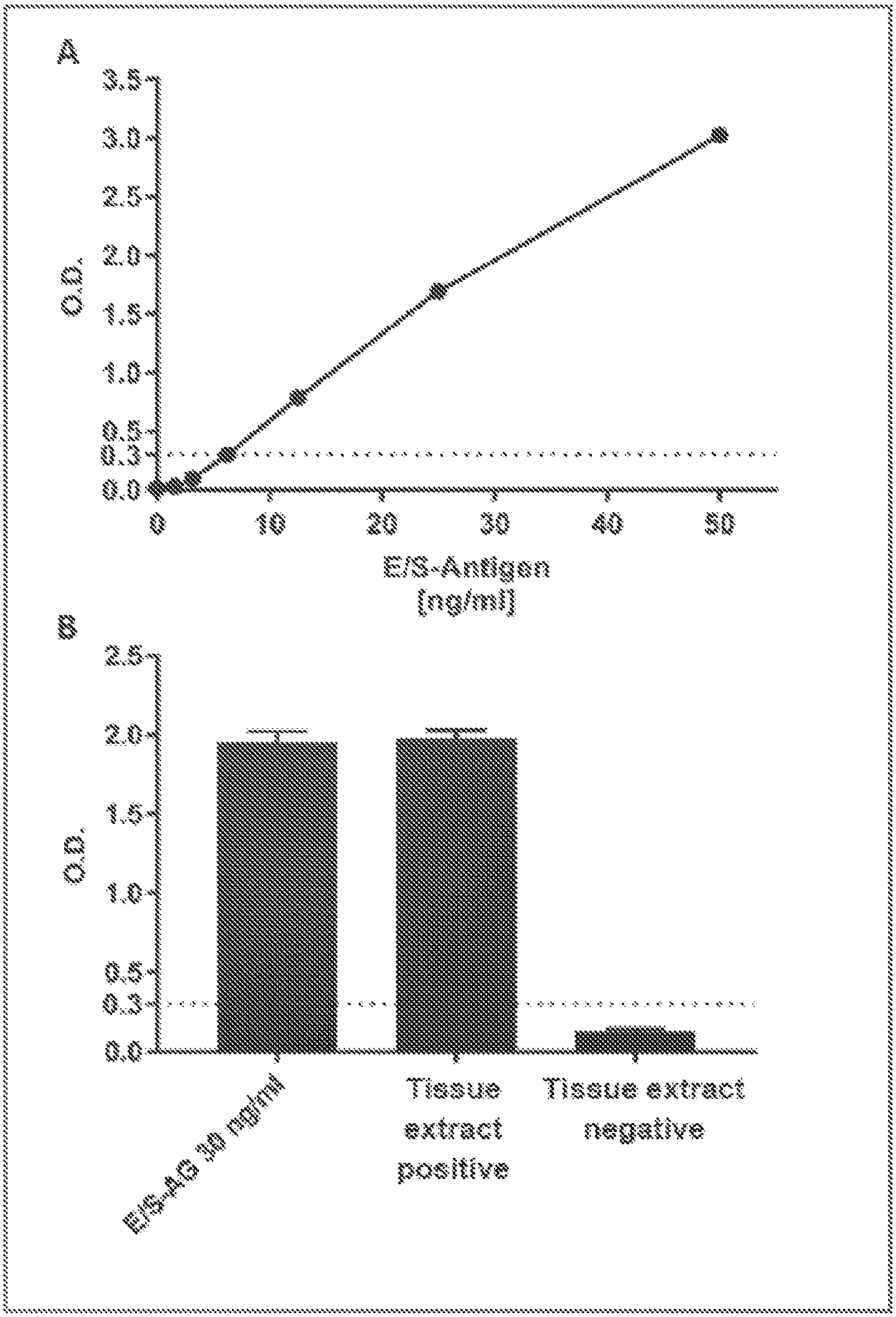
FIG. 7 shows results of the *T. spiralis* antigen capture ELISA. A) Detection limit of the *T. spiralis* antigen capture ELISA. Various concentrations of E/S antigen are plotted against the O.D. B) *T. spiralis* antigen capture ELISA with E/S antigen, positive and negative tissue extract as the sample material. The positive tissue extract sample contained approximately 100 encapsulated *Trichinella* larvae. Dashed line: Cut-off.

FIG. 7 shows results of the *T. spiralis* antigen capture ELISA. A) Detection limit of the *T. spiralis* antigen capture ELISA. Various concentrations of E/S antigen are plotted against the O.D. B) *T. spiralis* antigen capture ELISA with E/S antigen, positive and negative tissue extract as the sample material. The positive tissue extract sample contained approximately 100 encapsulated *Trichinella* larvae. Dashed line: Cut-off.

Figure 8:
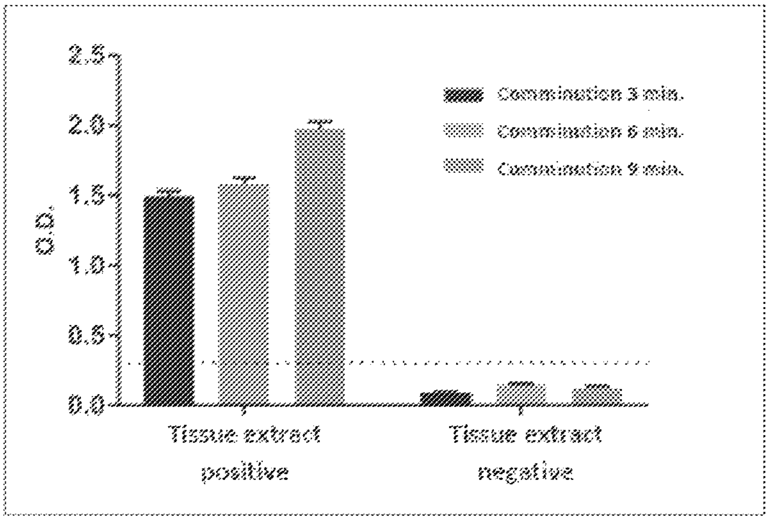
FIG. 8 shows results of the *T. spiralis* antigen capture ELISA with positive and negative tissue extract as the sample material. The positive tissue extract contained approximately 100 encapsulated *Trichinella* larvae. The sample material was comminuted for 3, 6, and 9 min. Dashed line: Cut-off. n=3.

FIG. 8 shows results of the *T. spiralis* antigen capture ELISA with positive and negative tissue extract as the sample material. The positive tissue extract contained approximately 100 encapsulated *Trichinella* larvae. The sample material was comminuted for 3, 6, and 9 min. Dashed line: Cut-off. n=3.

Figure 9:
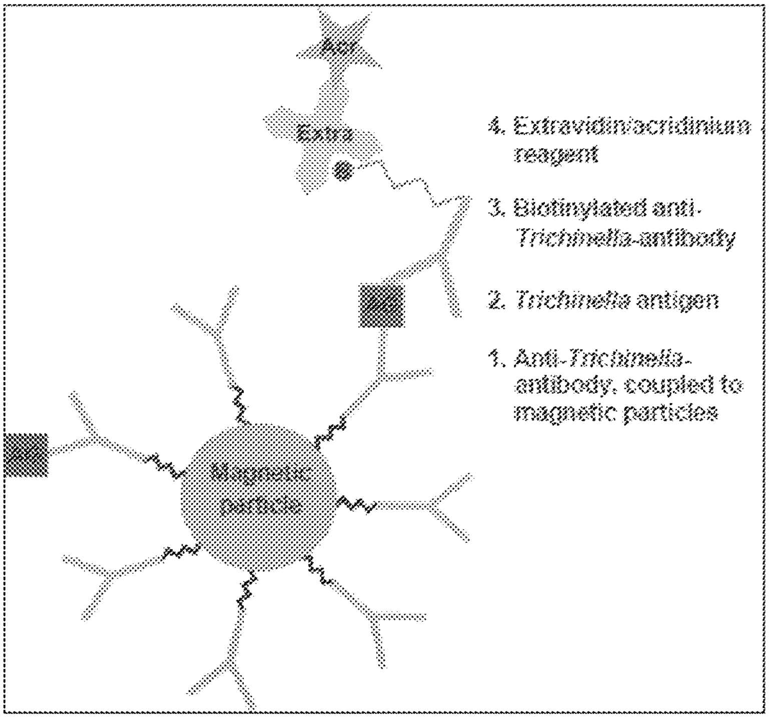
FIG. 9 shows an incubation schematic of the manually incubated *Trichinella* chemiluminescence immunoassay. 1) Anti-*Trichinella* capture Ab 18H1 immobilized on a magnetic bead, 2) Sample (*Trichinella* antigen), 3) Biotinylated anti-*Trichinella* detection Ab B7, 4) extravidin/acridinium reagent.

FIG. 9 shows an incubation schematic of the manually incubated *Trichinella* chemiluminescence immunoassay. 1) Anti-*Trichinella* capture Ab 18H1 immobilized on a magnetic bead, 2) Sample (*Trichinella* antigen), 3) Biotinylated anti-*Trichinella* detection Ab B7, 4) extravidin/acridinium reagent.

Figure 10:
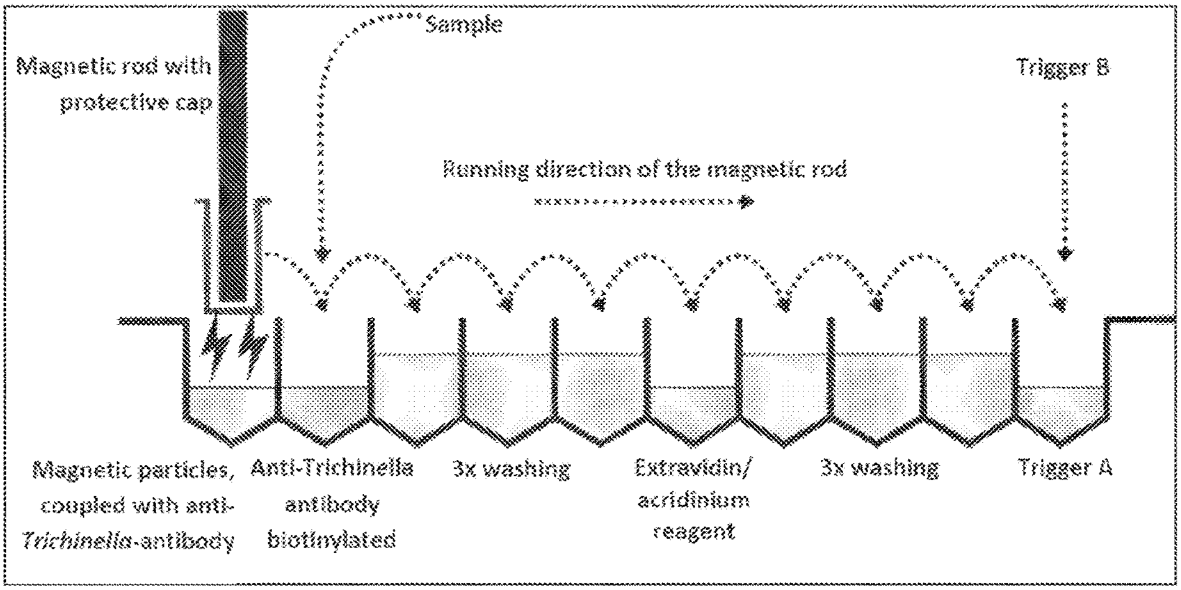
FIG. 10 shows the processing schematic of the chemiluminescence analyzer device for the automated *Trichinella* chemiluminescence immunoassay. The magnetic bar transports the beads immobilized with anti-*Trichinella* Ab 18H1 successively into reaction vessels filled with various reagents. The sample and trigger B are added automatically.

FIG. 10 shows the processing schematic of the chemiluminescence analyzer device for the automated *Trichinella* chemiluminescence immunoassay. The magnetic bar transports the beads immobilized with anti-*Trichinella* Ab 18H1 successively into reaction vessels filled with various reagents. The sample and trigger B are added automatically.

Figure 11:
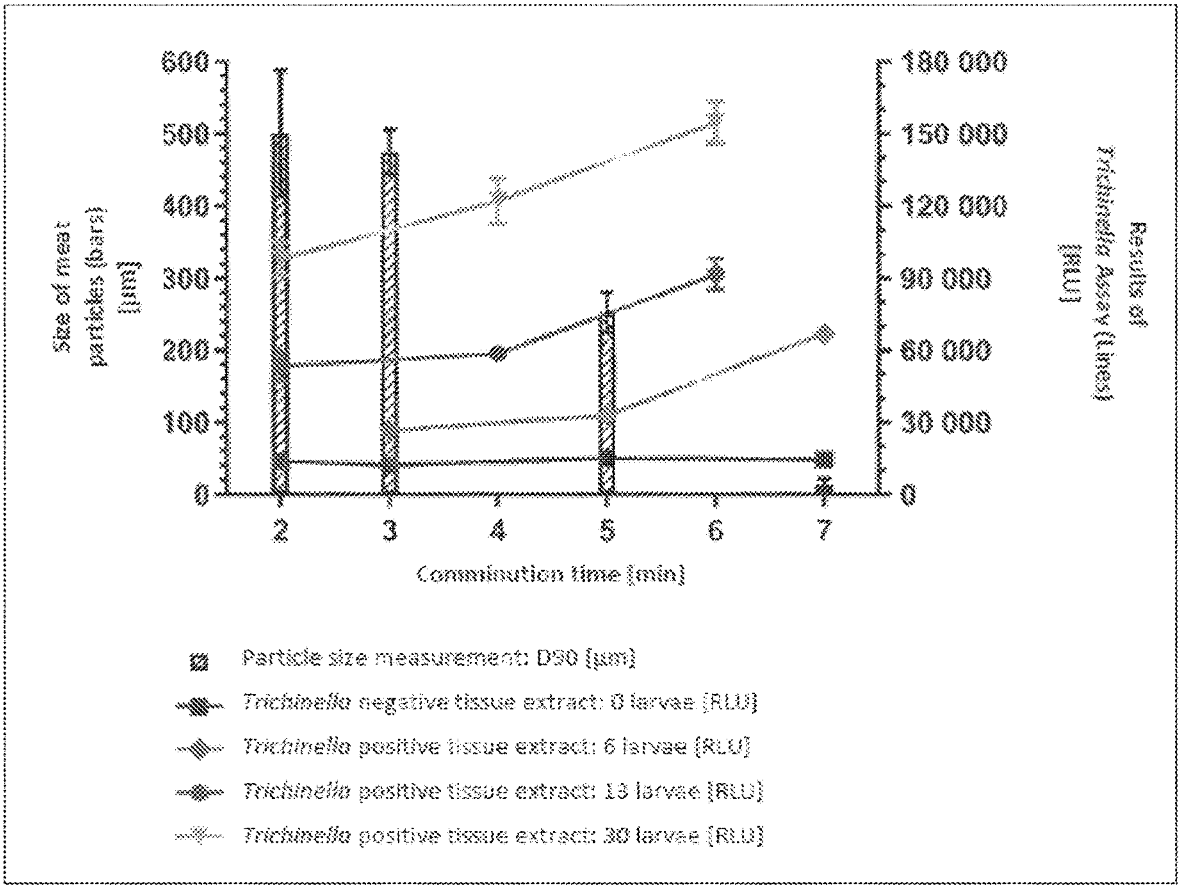
FIG. 11 shows results of the automated *Trichinella* chemiluminescence immunoassay. The particle sizes of the comminuted pork were measured after 2, 3, 5, and 7 min using the particle size analyzer LA-960 from HORIBA. In addition, meat samples—negative and mixed with 6, 13, and 30 *Trichinella* larvae—were comminuted between 2 and 7 min. The resulting tissue extract was incubated using the automated CLIA. The results are given in relative light units (RLU).

FIG. 11 shows results of the automated *Trichinella* chemiluminescence immunoassay. The particle sizes of the comminuted pork were measured after 2, 3, 5, and 7 min using the particle size analyzer LA-960 from HORIBA. In addition, meat samples—negative and mixed with 6, 13, and 30 *Trichinella* larvae—were comminuted between 2 and 7 min. The resulting tissue extract was incubated using the automated CLIA. The results are given in relative light units (RLU).

Sequences:

In the present invention, various peptide sequences are disclosed, in particular

```
(Anti-[TRISP][B7] VH):
                                          SEQ ID NO: 1
AVTLDESGGGLQTPRGGLSLVCKASGYTFSSHNMAWVRQAPGKGLEFVAG

ISNTGSFTLYGAAVKGRATISRDNGQSTVRLQLNNLRAEDTGTYYCAKHA

GVGLYSIDAWGHGTEVIVSS
```

-continued

```
(Anti-[TRISP][B7] VL):
                                          SEQ ID NO: 2
ALTQPSSVSANLGGTVKITCSGGTSDYGWYQQKAPGSAPVTLIYDNTNRP

SDIPSRFSGSLSGSTNTLTITGVQAEDEAVYFCGSADRTYAGVFGAGTTL

TVL

(ANTI-[TRISP][C9] VH):
                                          SEQ ID NO: 3
AVTLDESGGGLQTPGGALSLVCKASGFSISSYSMQWVRQAPGKGLEWVAG

IYYDGNTWYAPAVKGRATISRDNGQSTVRLRLNNLRAEDTATYFCAKYAG

GYSIDAWGHGTEVIVSS

(ANTI-[TRISP][C9] VL):
                                          SEQ ID NO: 4
ALTQPSSVSANPGETVKITCSGSSGSYGWYQQKSPGSGPVTVIYYNDKRP

SDIPSRFSGSASGSTATLTITGVQAEDEAVYFCGGYDSSTYVGIFGAGTT

LTVL

(ANTI-[TRISP][18H1] VH):
                                          SEQ ID NO: 5
QVQLKESGPGLVQPSQTLSLTCTVSGLSLTSNSVGWIRQPPGKGLEWMGI

IWSNGGIDYNSAIKSRLSISRDTSKSQVFLKMHSLQTEDTAMYFCARGPY

YGSYRLGYFDYWGQGVMVTVSS

(ANTI-[TRISP][18H1] VL):
                                          SEQ ID NO: 6
DVVMTQSPSSLAVSAGETVTLNCQSSQSLLYSGTQNNYLAWYQQKPGQSP

KLLISWASTRQSGVPLRFIGSGSGTDFTLTITSVQAEDLAIYYCQQFYDT

PLTFGSGTKLEIK
```

The present invention is further illustrated by the non-limiting examples, from which further features, embodiments, aspects, and advantages of the present invention can be derived.

EXAMPLES

Example 1: Material and Methods

Material

| Material | Name | Product number | Manufacturer |
|---|---|---|---|
| Equipment | Automated Chemiluminescent Analyzer SuperFlex | | PerkinElmer |
| | Biometra WT 15 042-400 shaker | | Biometra |
| | Centro $XS^3$ LB 960 Microplate Luminometer | | Berthold Technologies |
| | GM 200 Accessories: Grinding container, stainless steel | 03 045 0050 | Retsch |
| | GM 200 Accessories: Knife, serrated | 02 446 0057 | Retsch |
| | HydroFlex ™ Microplate Washer, Magnetic Beads | | Tecan |
| | Incubator WTB | | BINDER |
| | Knife mill GRINDOMIX GM 200 | 20 253 0001 | Retsch |
| | MTS 2/4 digital microtiter shaker | 3208001 | IKA |
| | Novex Mini Cell | | Invitrogen |
| | Photometer: Sunrise ™ | | Tecan |
| | Power Pac HV | | Bio-Rad |
| | Table centrifuge: Biofuge Fresco | | Heraeus |

-continued

| Material | Name | Product number | Manufacturer |
|---|---|---|---|
| | Washer Columbus | | Tecan |
| | XCell SureLock ™ Mini-Cell Electrophoresis System | | ThermoFisher Scientific |
| | Zentrifuge Avanti ® J-E (Rotor: JA-10) | | Beckman Coulter |
| | Tilt/roll mixer | | IKA |
| Consumables | iD PAGE Gel, 4-20% | ID-PA4201-015 | Eurogentec |
| | Dynabeads ™ M-280 Tosyl-activated | 14203 | ThermoFisher Scientific |
| | Microtiter plate LockWell Maxisorb | 446475-EUR | ThermoFisher Scientific |
| | Nitrocellulose membrane | 11306 | Sartorius |
| | Nunc ™ F96 MicroWell ™ Polystyrene Plate, white | 136101 | ThermoFisher Scientific |
| | Reagent Cartridges (SuperFlex) | | PerkinElmer |
| | Protective caps for magnetic rod (SuperFlex) | | PerkinElmer |
| Media, Solutions, and Buffers | Ammonium sulphate solution (3M) | | Sigma-Aldrich |
| | Antibody dilution buffer | | EUROIMMUN |
| | Blocking buffer ELISA | | EUROIMMUN |
| | Chromogen/substrate solution ELISA TMB/H2O2 | ZE 1200-0112 T | EUROIMMUN |
| | Enzyme Conjugate Alkaline Phosphatase-labeled Anti-Human-IgG (Goat) | AE 142 1030 | EUROIMMUN |
| | Extravidin/acridinium reagent | | EUROIMMUN |
| | Beads coating buffer | | EUROIMMUN |
| | PBS | ZF 1100-1000 T | EUROIMMUN |
| | PBS + 0.05% Tween-20 (PBST) | ZF 1110-0102 T | EUROIMMUN |
| | StabilCoat ® Plus | SC01 | Surmodics |
| | Stop solution ELISA (0.5M sulfuric acid) | ZE 1210-0112 T | EUROIMMUN |
| | Substrate Solution Blot Nitro Blue Tetrazolium Chloride/5-Bromo-4-chloro-3-indolyl Phosphate (NBT/BCIP) | ZW 1020-0130 T | EUROIMMUN |
| | Trigger A for CLIA | | EUROIMMUN |
| | Trigger B for CLIA | | EUROIMMUN |
| | Tris buffer (1M) | #1218 | Gerbu Biotechnik |
| | Wash Buffer Blot | ZW 1100-1005 T | EUROIMMUN |
| | Wash Buffer ELISA | ZE 1120-1000 T | EUROIMMUN |
| | Wash Buffer Plus Blot | ZW 1110-1005 | EUROIMMUN |
| Ready-to-use Solutions and Kits | Color Prestained Protein Standard, Broad Range (11-245 kDa) | P7712S | New England BioLabs |
| | NuPAGE ® LDS Sample Buffer (4×) | | ThermoFisher Scientific |
| | NuPAGE ™ MOPS SDS Running Buffer (20×) | NP0001 | ThermoFisher Scientific |
| Antigens | *Ascaris suum* | | Prof. Dr. Christina Strube, University of Veterinary Medicine Hanover, DE |
| | *Salmonella typhimurium* | | Prof. Dr. Michael |
| | *Salmonella cholerasuis* strain A | | Hensel microbiology |
| | *Salmonella cholerasuis* strain B | | University of Osnabrück |
| | *Salmonella typhisuis* | | |
| | *Strongyloides ratti* | | EUROIMMUN |
| | *Toxocara cati* | | EUROIMMUN |
| | *Toxoplasma gondii* | BA110VS | Virion/Serion |
| | *Trichinella spiralis* E/S antigen | | EUROIMMUN |
| | *Trichinella spiralis* lysate | | EUROIMMUN |
| | *Trichuris suis* | | Prof. Dr. Eva Liebau Molecular Physiology University of Münster |
| | *Trypanosoma cruzi* | | Virion/Serion |

-continued

| Material | Name | Product number | Manufacturer |
|---|---|---|---|
| Antibodies | Anti-[TRISP][B7] | | EUROIMMUN |
| | Anti-[TRISP][C9] | | EUROIMMUN |
| | Anti-[TRISP][18H1] | | EUROIMMUN/Prof. Dr. Judith Appleton, Cornell University, Ithaca, USA |
| Other Materials | EZ-Link ™ NHS-PEG12 biotin | 21312 | ThermoFisher Scientific |
| | IIFT *Trichinella spiralis* "Encapsulated Larva" | | EUROIMMUN |
| | IIFT *Trichinella spiralis* "Muscle larva" | | EUROIMMUN |
| | Pork samples mixed with a defined number of *Trichinella* muscle larvae | | [German] Federal Institute for Risk Assessment (BfR) |
| | Pork diaphragm muscles | | Butcher Prösch, Krummesse |
| | Spectra ™ Multicolor Broad Range Protein Ladder | | ThermoFisher Scientific |
| | Streptavidin-PolyHRP80, stock 1 mg/ml solution | #SP80C | SDT (Stereospecific Detection Technologies) |
| | Trichinous pork infected with 20 to 50 larvae per gram | | [German] Federal Institute for Risk Assessment (BfR) |
| | Zeba ™ Spin Desalting Columns, 40K MWCO, 10 mL | 87772 | ThermoFisher Scientific |

Methods

Method for Obtaining Tissue Extract Samples

In the present detection method, the meat is not supposed to be enzymatically digested, but rather mechanically comminuted. In this regard, a particle size of the meat of <200 μm is to be achieved. The larvae, together with the collagen capsule, are approx. 200-600 μm long and 200-300 μm wide, so that with a desired particle size of <200 μm, it can be assumed that the encapsulated *Trichinella* larvae would have to be caught at least once by the cutting knife of the comminution device. The capsule contains numerous E/S proteins, which are released during comminution and then freely present in the sample material (FIG. 1). The somatic proteins can be additionally detected by the comminution of the larva.

Following comminution, antigen detection is performed in the form of an antigen capture ELISA or a manually incubated or automated chemiluminescence immunoassay.

Sample Preparation

At the slaughterhouse, removal of about 5 g of meat per animal is usual. As a standard procedure, the sample is taken from the muscular part of the diaphragm of an animal that has already been killed. For the *Trichina* inspection, 1 g of sample material is used per pig. For other parts of the body, such as the tongue or intercostal muscles, the amount of the sample may vary. As a rule, 100 pig samples are pooled, resulting in a sample volume of 100×1 g. The sample is cooled down to 4° C.

Comminution of the Meat Samples

The sample material (100×1 g meat) was added to the grinding bowl of a crusher, which was pre-chilled to 4° C. The knife mill Grindomix GM 200 from Retsch was used for this purpose. The comminution principle is based on cutting of the sample. The knife mill can be equipped with a serrated knife, so that even fibrous materials such as muscle tissue can be finely comminuted. 200 ml of PBS at a temperature of 4° C. were added to the sample. At 10,000 rpm and thus maximum power, the sample material was comminuted as indicated, e.g. for 9 min.

In order to check whether comminution of the meat was successful, a particle size measurement was carried out using the Camsizer®XT from Retsch and the LA-960 from HORIBA. The LA-960 is based on the functional principle of static laser scattering, whereas the Camsizer®XT is based on dynamic image analysis. In each case, three meat samples were taken after 6 minutes or 9 minutes, and measured directly afterwards. An average of 60 million particles were measured. The particle size was measured in $x_{c\ min}$ and defined according to DIN 66141 as follows: Shortest particle diameter of the measurements of the maximum diameter within a particle projection (English: particle diameter which is the shortest chord of the measured set of maximum chords of a particle projection) [8].

Centrifugation

After comminution, 1 ml to 15 ml of sample were taken from the grinding bowl using a pipette. This was followed by sedimentation of the coarse particles in the sample by centrifugation at 5,000×g and 4° C. for 10 minutes. The supernatant after sedimentation is the sample material for subsequent antigen detection and is referred to as a tissue extract.

Method of Detecting *Trichinella spiralis* from Tissue Extract Samples

Production of the Sample Material

*T. spiralis* Lysate

*T. spiralis* muscle larvae (ML) were provided by Justyna Bień from the Witold Stefański Institute PAS in Warsaw. 120,000 ml were centrifuged for 10 min at 16,000×g and room temperature (RT), so that all larvae were pelleted. The supernatant was discarded and 1 ml of PBS was added. The larvae were exposed to five cycles of freezing and thawing, and then comminuted using a hand-held homogenizer. Finally, the samples were treated with ultrasound: 20 cycles of 5 sec each at medium strength and 5 sec rest periods between treatments, on ice. This was followed by 20 minute centrifugation at 16,000×g and 4° C. The supernatant represents the antigen *T. spiralis* lysate.

E/S Antigen

The *T. spiralis* ML E/S antigen was provided by Justyna Bień from the Witold Stefański Institute PAS in Warsaw.

Production of Antibodies

The antibodies used for the antigen-capture ELISA were prepared using a phage display method [9]. The sequences of the heavy and light chain variable regions (VH and VL) of the two antibodies anti-[TRISP][B7] and anti-[TRISP][C9] (abbreviated as Ab B7 and Ab C9) are as follows:

```
Anti-[TRISP][B7] VH (SEQ ID NO: 1):
AVTLDESGGGLQTPRGGLSLVCKASGYTFSSHNMAWVRQAPGKGLEFVAG

ISNTGSFTLYGAAVKGRATISRDNGQSTVRLQLNNLRAEDTGTYYCAKHA

GVGLYSIDAWGHGTEVIVSS

Anti-[TRISP][B7] VL (SEQ ID NO: 2):
ALTQPSSVSANLGGTVKITCSGGTSDYGWYQQKAPGSAPVTLIYDNTNRP

SDIPSRFSGSLSGSTNTLTITGVQAEDEAVYFCGSADRTYAGVFGAGTTL

TVL

ANTI-[TRISP][C9] VH (SEQ ID NO: 3):
AVTLDESGGGLQTPGGALSLVCKASGFSISSYSMQWVRQAPGKGLEWVAG

IYYDGNTWYAPAVKGRATISRDNGQSTVRLRLNNLRAEDTATYFCAKYAG

GYSIDAWGHGTEVIVSS

ANTI-[TRISP][C9] VL (SEQ ID NO: 4):
ALTQPSSVSANPGETVKITCSGSSGSYGWYQQKSPGSGPVTVIYYNDKRP

SDIPSRFSGSASGSTATLTITGVQAEDEAVYFCGGYDSSTYVGIFGAGTT

LTVL
```

Biotinylation of Antibody Anti-[TRISP][B7]

The Ab B7 was incubated, for antigen-capture ELISA, using EZ-Link™ NHS-PEG12-biotin in a 20-times molar excess, for one hour at room temperature, on the rotary shaker. To remove excess biotin, the antibody (Ab) was purified according to the manufacturer's instructions, by way of a size exclusion chromatography column (Zeba™ Spin Desalting Columns).

SDS PAGE and Western Blot Analysis

For SDS PAGE, in each case 5 μg of *T. spiralis* lysate or lysate from *Trypanosoma cruzi, Ascaris suum, Strongyloides ratti, Toxocara cati, Toxoplasma gondii, Salmonella typhimurium, Salmonella cholerasuis* strain A, *Salmonella cholerasuis* strain B, *Salmonella typhisuis*, and *Trichuris suis* were loaded onto a polyacrylamide gel, and electrophoresis was performed at 175V in MOPS buffer for 50 min. Transfer to a nitrocellulose membrane took place for 60 min at 400 mA, in transfer buffer. The membrane was incubated for blocking on the rocker shaker, in Wash Buffer Plus, for 30 min. Subsequently, antibodies B7 and C9 in Wash Buffer Plus were applied at a concentration of 0.4 μg/ml, and incubated overnight on the rocker shaker. After washing with washing buffer, the membrane was incubated with the enzyme conjugate "Alkaline Phosphatase-labeled Anti-Human IgG" from EUROIMMUN, diluted in Wash Buffer Plus. Finally, after another washing step, the substrate solution (NBT/BCIP) was applied and incubated until a clear color change was seen.

Indirect Immunofluorescence Test

In order to examine which structures bind the developed antibodies, an indirect immunofluorescence test for *T. spiralis* was developed. The BIOCHIPS were loaded with frozen sections of *T. spiralis* muscle larvae and encapsulated larvae. Incubation and microscopy were carried out following the instructions of the EUROIMMUN Anti-Schistosoma Mansoni IIFT (P/N FI 2300-1005 G). As a sample, the antibodies B7 and C9 were applied to the BIOCHIPS at a concentration of 2 μg/ml.

Antigen Detection by Means of Antigen Capture ELISA

For antigen detection, an enzyme-linked immunosorbent assay (ELISA) was used as the detection method. A 96-well microtiter plate was coated with 0.25 μg/ml antibody C9 in PBS overnight at 4° C. The next day, the microtiter plate was washed once with PBST (PBS+0.05% Tween-20), blocked with blocking buffer for 2 hours, and then dried for 2 hours.

For detection of the antigens bound to Ab C9, the Ab B7, at a concentration of 0.05 μg/ml, and streptavidin-polyHRP80, at a concentration of 0.1 μg/ml, were mixed together in antibody dilution buffer and incubated overnight.

Incubation of the Samples

The incubation was carried out as in the schematic shown in FIG. 2. As samples, the *T. spiralis* E/S antigen, at various concentrations (0-50 ng/ml), and tissue extract samples in a volume of 100 μl were applied to the microtiter plate. The incubation was carried out for one hour at room temperature, on a rotary shaker. The "positive" tissue extract sample was prepared in that before comminution, trichinous pork was added to negative diaphragm tissue, so that there were approximately 100 encapsulated *Trichinella* larvae in the sample.

After washing with washing buffer six times, the 100 μl volume conjugate was also incubated for one hour at room temperature, on a rotary shaker. It was then washed again six times and the substrate was applied. After 15 min, the reaction was stopped with stop solution, and the optical density (O.D.) of the samples was determined using a photometer at a wavelength of 450 nm.

Example 2: Results

Comminution of the Meat Samples

Immediately following comminution of the pork using the GM200 knife mill, particle size determination was carried out using the Camsizer®XT and the HORIBA LA-960. Sampling took place after 6 or 9 min, respectively. The results of the mass distribution can be seen in FIG. 3, where the particle size [μm] is plotted against Q3 [%] in a diagram. Q3 is the percentage of particles that are smaller than x with reference to the total volume. Since the two particle size measuring devices are based on different measuring methods, the results differ.

The results of the measurement with the HORIBA LA-960 show that 95% of the particles are <26 μm and all particles are <100 μm. With the Camsizer®XT measurement, 95% of the particles are <300 μm. Only 70% of the meat particles are <100 μm. FIG. 4 shows, as an example, what shape the meat particles have. Due to the muscle fibers and myofibrils, the structure is very fibrous, which clearly lowers the width to length ratio.

In any case, the collagen capsule of a *Trichinella* larva, if present, would be statistically cut at least once by the knife, so that E/S proteins can be released. These released proteins can be detected in the next step, using an antigen-capture ELISA.

Preparation of the Sample Material and the Antibodies

To check whether the antibodies anti-[TRISP][B7] and anti-[TRISP][C9] are suitable for *T. spiralis* antigen detection, an indirect immunofluorescence test (IIFT) and a Western blot were performed as functional tests. The results are shown in FIG. 5.

When antibody B7 is used, the cut capsule fluoresces most strongly (FIG. 5 A). The larva inside and individual proteins on the capsule surface also fluoresce. The frozen section of the muscle larva shows a clear reaction at the outer membrane (FIG. 5 B).

In the cross-section of the encapsulated larva, the entire larva fluoresces most strongly when incubated with the Ab C9 (FIG. 5 C). The individual proteins on the capsule surface and the cut capsule fluoresce weakly. In the case of the muscle larva, not only does the outer membrane show a clear reaction, but the inside of the larva does also (FIG. 5 D).

In the Western blot, clear reactions for the antibodies B7 and C9 can also be seen (FIG. 5 E). The two antibodies show an identical band pattern. Strong bands occur at approximately 48, 50, 52, 60, 65, and 110 kDa. The epitope bound by the antibodies seems to be present in several proteins or glycoproteins, and this may have a positive effect on the detection of very low-concentration *Trichinella* antigens in the sample material.

In order to check whether the antibodies bind exclusively to specific structures of *T. spiralis* and not to other antigen structures of other parasites and/or bacteria, a Western blot was performed. Lysates of pathogens found in pigs were applied. The result can be seen in FIG. 6. The lysates tested possess no structures bound by Ab B7 or Ab C9. A false positive reaction can be excluded for these pathogens, with high probability, in the later antigen capture ELISA.

Antigen Capture ELISA

For the functional test of the developed *T. spiralis* ELISA, various concentrations of E/S antigen were used in the test (FIG. 7 A). The detection limit, at a cutoff of 0.3 O.D., lies at approximately 6 ng/ml.

In FIG. 7 B, results of tissue extract samples prepared according to the procedure described herein were shown. Both a positive sample, containing about 100 encapsulated larvae in the pork, and a negative sample were tested. The antigen capture ELISA shows a clear difference of almost 2 O.D. between the positive and the negative tissue extract sample.

The *T. spiralis* antigen concentration in the tissue extract sample corresponds to approximately 30 ng/ml E/S antigen. Consequently, 100 comminuted encapsulated larvae release approximately that amount of protein into the meat juice, and this can be detected by the antigen capture ELISA.

Antigen-Capture ELISA with Differently Comminuted Sample Material

FIG. 8 shows the results of comminution, after 3, 6, and 9 min, of positive and negative tissue extract. It can be seen that the negative tissue extract without larvae in the sample material shows no significant reaction, since the O.D. in ELISA lies below the cut-off of 0.3. The tissue extract that was produced from meat and contained approximately 100 encapsulated *T. spiralis* larvae shows a clear reaction at >1.5 O.D. The effects resulting from the scope of comminution are conspicuous, since the reaction increases with an increasing comminution time. The O.D. in the case of the 9-minute comminution is 0.5 higher than in the case of the 3-minute comminution.

The reaction in the ELISA is lower in the case of the sample material which was comminuted for 3 minutes than after comminution for 9 minutes. Prolonged comminution of the sample material consequently results in a higher amount of released *T. spiralis* antigen. During prolonged comminution, it is likely that all encapsulated *Trichinella* larvae will be caught at least once and, in general, multiple times by the cutter blade, so that more detectable antigens are available for ELISA in the sample, as compared with shortened comminution.

Example 3: Antigen Detection by Means of a Manually Incubated and Automated Chemiluminescence Immunoassay For the manually incubated and bead-based chemiluminescence immunoassay (CLIA), the capture antibodies were coupled to magnetic beads rather than to a microtiter plate. Tosyl-activated Dynabeads™ were used for this purpose. The hydrophobic polyurethane surface was activated with tosyl groups, which allowed the antibodies to be covalently bound to the beads. 4 mg of the beads were equilibrated with 1 ml of a 1 M Tris buffer. 30 mM Tris, 0.4 M ammonium sulfate, and 28 μg anti-[TRISP][18H1] antibody (abbreviated as Ab 18H1) were added to the equilibrated beads. The incubation was carried out overnight at 37° C., on a roller mixer. The next day, the beads were washed three times with 1 ml each of StabilCoat® Plus, and then incubated overnight at 37° C., on the roller mixer, to block any remaining reactive functional groups. After blocking, the beads were taken up in fresh StabilCoat® Plus and stored at a concentration of 1 mg/ml at 4° C. until use.

The beads coated with 18H1 antibody were pipetted into a microtiter plate well (Nunc™ polystyrene plate) for the CLIA, at 10 μg each. 100 μl of the undiluted tissue extract sample were added, and incubated for 30 min on a rotary shaker. After automated washing three times using the HydroFlex™ Microplate Washer, 100 μl of the biotinylated B7 antibody at a concentration of 0.1 μg/ml were incubated for 30 minutes on a rotary shaker. This was followed by three times automated washing. For the chemiluminescence reaction, the extravidin/acridinium reagent, at a concentration of 80 ng/ml and a volume of 100 μl, was added to the beads and incubated for 15 min. After washing three times, the measurement was carried out using the Centro $XS^3$ microplate luminometer. The luminometer automatically added 100 μl of each of the triggers A and B to every batch, to start the chemiluminescence reaction. The light emission was measured at 425 nm wavelength for 1 sec and reported in Relative Light Units (RLU). The incubation schematic of the manually incubated CLIA is shown in FIG. 9.

The automated and bead-based chemiluminescence immunoassay is based on the structure of the manually incubated CLIA. The difference is that the test is performed using an Automated Chemiluminescence Analyzer (SuperFlex, PerkinElmer). The beads are successively immersed in the various reagents by a magnetic rod. The magnetic rod is able to generate an electric field and can thereby pick up the beads, drop them, and mix the reagents at a predefined interval.

For the automated CLIA, the tissue extract samples were loaded into the sample compartment of the analyzer. The reagent cartridges were filled as shown in FIG. 10. Per reaction, 10 μg of the beads coated with 18H1 antibody were used. These were incubated with 100 μl of tissue extract sample and 100 μl of biotinylated anti-TRISP[B7] antibody at a concentration of 0.25 μg/ml for 30 min. The beads were taken up with the magnetic bar after incubation, and washed 3 times in washing buffer (V=400 μl). This was followed by a 10-minute incubation with 100 μl of 0.1 μg/ml extravidin/acridinium reagent. After being washed three times, the beads were added to 100 μl of Trigger A, and Trigger B (V=100 μl) was pipetted in by the analyzer to start the chemiluminescence reaction. The light emission was measured at 425 nm wavelength for 1 sec by the luminometer built into the analyzer, and reported in Relative Light Units (RLU).

Results of the Manually Incubated Chemiluminescence Immunoassay (CLIA)

Different concentrations of *T. spiralis* lysate samples were incubated with the manually incubated CLIA. The detection limit was 1 ng/ml *T. spiralis* lysate.

Results of the Automated Chemiluminescence Immunoassay (CLIA)

Different concentrations of *T. spiralis* lysate samples were also incubated using the automated chemiluminescence immunoassay. The detection limit was 10 µg/ml *T. spiralis* lysate. In addition to the meat samples infected with *Trichinella*, meat samples that were mixed with a defined amount of *Trichinella* muscle larvae were also comminuted. They contained 3 to 30 larvae. The detection limit of the automated CLIA was 3 larvae per 100 grams of meat for the defined amount of muscle larvae.

FIG. 11 shows the correlation between particle size and the results of CLIA of comminuted and *Trichinella*-positive tissue extract. It can be seen that the particle size of the meat decreases with an increasing comminution time, whereas the reaction of the CLIA increases. With progressive comminution of the meat, and thus also of the larvae, more *Trichinella* antigens are released. These can then be detected by the CLIA. The relative light units (RLU) also increase with an increasing number of larvae in the meat sample. The *Trichinella*-positive tissue extract from meat samples mixed with 30 larvae shows more than three times as high a reaction (150,000 RLU) than the tissue extract of 6 larvae (50,000 RLU) after 6 min comminution.

The invention is described generically and generally herein. Each of the narrower types and subgroups covered by the generic disclosure also forms part of the invention. This includes the general description of the invention with a reservation or negative restriction that removes every object from a (sub)group, whether or not the cut-out object is specifically cited here. Other embodiments are contained in the following claims.

A person skilled in the art will readily appreciate that the present invention is well suited for accomplishing the tasks and achieving the stated advantages and goals connected with them. Furthermore, it will be readily apparent to a person skilled in the art that various substitutions and modifications can be made to the invention disclosed herein, without departing from the scope and spirit of the invention. The methods, uses, treatments, molecules, and kits described herein are representative of preferred embodiments, which are exemplary and are not intended to restrict the scope of the invention. Changes therein and other uses will occur to persons skilled in the art, and these are included within the scope of the invention and defined by the scope of the claims. Listing or discussion of a previously published document in this description should not necessarily be understood as proof that the document belongs to the prior art or is generally known.

The invention illustratively described herein can be suitably carried out in the absence of any element or restrictions not specifically disclosed herein. For example, the terms "comprising," "including," "containing," etc., are read comprehensively and without restriction. Accordingly, the word "comprise" or variations such as "comprises" or "comprising" are to be understood as being implicit; i.e., for example, numbers that are given are included, but not excluded. In addition, the terms and expressions used herein have been used as expressions of description and not of restriction, and there are no intentions to restrict such terms and expressions, so as to restrict any equivalents of the features shown or described, or parts thereof. In other words, various modifications are possible within the scope of protection of the claimed invention. This should be understood to mean that while the present invention has been specifically disclosed by means of exemplary embodiments and optional features, which are disclosed herein, modifications and variations of the inventions disclosed herein can be used by persons skilled in the art, and that such modifications and variations should be viewed as being within the scope of protection of this invention.

The contents of all documents and patent documents cited herein are incorporated by reference, in their entirety.

Abbreviations

| Abbreviation | English | German |
|---|---|---|
| µg | microgram | Mikrogramm |
| µl | microliter | Mikroliter |
| German: AG English: Ag | antigen | Antigen |
| German: AK English: Ab | antibody | Antikörper |
| CLIA | Chemiluminescence Immunoassay | Chemilumineszenz Immunassay |
| E/S | Excretory/Secretory | Exkretorisch/Sekretorisch |
| ELISA | Enzyme-linked Immunosorbent Assay | |
| EU | European Union | Europaische Union |
| g | gram | Gramm |
| IIFT | indirect immono-fluorescence test | Indirekter Immunfluoreszenztest |
| l | liter | Liter |
| mg | milligram | Milligramm |
| Min. | minute | Minute |
| ml | milliliter | Milliliter |
| ML | muscle larva | Muskellarven |
| NBL | New Born Larva | Neugeborene Larven |
| NBT/BCIP | nitro-blue tetrazolium chloride/5-bromo-4-chloro-3-indolylophos-phate p-toluidine salt | Nitroblautetrazoliumchlorid/5-Brom-4-chlor-3-indolylphosphat |
| Ng | nanogram | Nanogramm |
| nm | nanometer | Nanometer |
| O.D. | Optical Density | Optische Dichte |
| rpm | revolutions per minute | Umdrehungen pro Minute |
| RT | room temperature | Raumtemperatur |
| Sek. | second | Sekunde |
| SDS PAGE | Sodium Dodecyl Sulfate Polyacrylamide Gel Electrophoresis | Natriumdodecylsulfat-Polyacrylamidgel-elektrophorese |

LITERATURE

1. Dupouy J, Murrell K D: FAO/WHO/OIE guidelines for the surveillance, management, prevention and control of trichinellosis; 2007.
2. Mitreva M, Jasmer D P: WormBook: Biology and genome of *Trichinella spiralis;* 2006.
3. Zarlenga D S, La Rosa G, Pozio E, Rosenthal B: Identification and classification within the genus *Trichinella*, with special emphasis on non-encapsulated species. *Vet Parasitol* 2004, 125: 75-78.
4. Liu M, Boireau P: Trichinellosis in China: epidemiology and control. *Trends Parasitol* 2002, 18(12): 553-556.
5. BfR [German Federal Institute for Risk Assessment]: Trichinellose—Erkennung, Behandlung und Verhütung [Trichinellasis—detection, treatment, and prevention]. *Information BfR* 2007 [Information from the BfR, 2007].

6. Kapel C M: Changes in the EU legislation on *Trichinella* inspection—new challenges in the epidemiology. *Vet Parasitol* 2005, 132 (1-2): 189-194.
7. Nöckler K, Serrano F J, Boireau P, Kapel C M, Pozio E: Experimental studies in pigs on *Trichinella* detection in different diagnostic matrices. *Vet Parasitol* 2005, 132(1-2): 85-90.
8. RKI [Robert Koch Institute]: Ringversuch zum Nachweis von Trichinellen in Fleisch [collaborative trial to detect *Trichinella* in meat]. In: Robert Koch Institute; 2016.
9. Report on the Validation of the Trichin-L antigen test kit of the Bio-Rad Company In: European Union Reference Laboratory for Parasites; 2010.
10. Retsch GmbH: CAMSIZER® Characteristics—Basis of definition DIN 66141. 2009.
11. Appleton J A, Schain L R, and McGregor D D. 1988. Rapid expulsion of *Trichinella spiralis* in suckling rats: mediation by monocional antibodies. Immunology 65: 487-492.
12. Altschul S F, Gish W, Miller W, Myers E W & Lipman D J. (1990) Basic local alignment search tool. J. Mol. Biol. 215: 403-410
13. Altschul S F, Madden T L, Schaffer A A, Zhang J, Zhang H, Miller W, and Lipman D J. (1997): Gapped BLAST and PSI-BLAST: a new generation of protein database search programs; Nucleic Acids Res., 25, pp. 3389-3402
14. Chenna et al. (2003): Multiple sequence alignment with the Clustal series of programs. Nucleic Acid Research 31, 3497-3500
15. Notredame et al. (2000): T-Coffee: A novel method for multiple sequence alignments. J. Mol. Biol. 302, 205-217

The invention claimed is:

1. A method of detecting *Trichinella* in a tissue extract sample, said method comprising:

comminuting the tissue extract sample from a human or animal to form particles, wherein at least 90% of the particles have a diameter of 6 μm to 300 μm; and detecting an antigen of *Trichinella* in said tissue extract sample by detecting the binding between an antibody to the antigen of *Trichinella* and the antigen, wherein the antigen is at least one of tyvelose, an excretory-secretor antigen, and a *Trichinella spiralis* lysate, wherein the detecting comprises:

contacting the particles with a first antibody that is bound to one of beads, a membrane, a microtiter plate, a slide, a filter material, a thin layer chromatography material, and a test strip, wherein the first antibody recognizes the antigen of *Trichinella;* contacting the particles with a second antibody that recognizes the antigen of *Trichinella*, the second antibody being bound to a signal molecule; and detecting the antigen of *Trichinella* via the signal molecule.

2. The method according to claim 1, wherein the tissue extract sample is a mammalian sample.

3. The method according to claim 1, wherein 90% of the particles in the tissue extract sample have a diameter of 250 μm or less.

4. The method according to claim 1, wherein the tissue extract sample is from musculature of said human or animal.

5. The method according to claim 1, wherein in the preparation of the tissue extract sample (a) a temperature of 45° C. is not exceeded; and/or (b) no enzymatic and/or chemical cleavage of the tissue takes place.

6. The method according to claim 1, wherein the method (a) does not comprise a microscopy step;

(b) is used in meat inspection; and/or (c) has a detection limit of ≤7 ng antigen per ml of tissue extract.

7. The method according to claim 1, wherein the method is performed by an immunoassay.

8. The method according to claim 1, wherein *Trichinella* is *Trichinella spiralis*.

* * * * *

```
                              SEQUENCE LISTING

<160> NUMBER OF SEQ ID NOS: 6

<210> SEQ ID NO 1
<211> LENGTH: 120
<212> TYPE: PRT
<213> ORGANISM: Artificial Sequence
<220> FEATURE:
<223> OTHER INFORMATION: Anti-[TRISP][B7] VH

<400> SEQUENCE: 1

Ala Val Thr Leu Asp Glu Ser Gly Gly Gly Leu Gln Thr Pro Arg Gly
1               5                   10                  15

Gly Leu Ser Leu Val Cys Lys Ala Ser Gly Tyr Thr Phe Ser Ser His
            20                  25                  30

Asn Met Ala Trp Val Arg Gln Ala Pro Gly Lys Gly Leu Glu Phe Val
        35                  40                  45

Ala Gly Ile Ser Asn Thr Gly Ser Phe Thr Leu Tyr Gly Ala Ala Val
    50                  55                  60

Lys Gly Arg Ala Thr Ile Ser Arg Asp Asn Gly Gln Ser Thr Val Arg
65                  70                  75                  80

Leu Gln Leu Asn Asn Leu Arg Ala Glu Asp Thr Gly Thr Tyr Tyr Cys
                85                  90                  95

Ala Lys His Ala Gly Val Gly Leu Tyr Ser Ile Asp Ala Trp Gly His
            100                 105                 110

Gly Thr Glu Val Ile Val Ser Ser
        115                 120


<210> SEQ ID NO 2
<211> LENGTH: 103
<212> TYPE: PRT
<213> ORGANISM: Artificial Sequence
<220> FEATURE:
<223> OTHER INFORMATION: Anti-[TRISP][B7] VL

<400> SEQUENCE: 2

Ala Leu Thr Gln Pro Ser Ser Val Ser Ala Asn Leu Gly Gly Thr Val
1               5                   10                  15

Lys Ile Thr Cys Ser Gly Gly Thr Ser Asp Tyr Gly Trp Tyr Gln Gln
            20                  25                  30

Lys Ala Pro Gly Ser Ala Pro Val Thr Leu Ile Tyr Asp Asn Thr Asn
        35                  40                  45

Arg Pro Ser Asp Ile Pro Ser Arg Phe Ser Gly Ser Leu Ser Gly Ser
    50                  55                  60
```

-continued

```
Thr Asn Thr Leu Thr Ile Thr Gly Val Gln Ala Glu Asp Glu Ala Val
65                  70                  75                  80

Tyr Phe Cys Gly Ser Ala Asp Arg Thr Tyr Ala Gly Val Phe Gly Ala
                85                  90                  95

Gly Thr Thr Leu Thr Val Leu
            100


<210> SEQ ID NO 3
<211> LENGTH: 117
<212> TYPE: PRT
<213> ORGANISM: Artificial Sequence
<220> FEATURE:
<223> OTHER INFORMATION: ANTI-[TRISP][C9] VH

<400> SEQUENCE: 3

Ala Val Thr Leu Asp Glu Ser Gly Gly Gly Leu Gln Thr Pro Gly Gly
1               5                   10                  15

Ala Leu Ser Leu Val Cys Lys Ala Ser Gly Phe Ser Ile Ser Ser Tyr
            20                  25                  30

Ser Met Gln Trp Val Arg Gln Ala Pro Gly Lys Gly Leu Glu Trp Val
        35                  40                  45

Ala Gly Ile Tyr Tyr Asp Gly Asn Thr Trp Tyr Ala Pro Ala Val Lys
    50                  55                  60

Gly Arg Ala Thr Ile Ser Arg Asp Asn Gly Gln Ser Thr Val Arg Leu
65                  70                  75                  80

Arg Leu Asn Asn Leu Arg Ala Glu Asp Thr Ala Thr Tyr Phe Cys Ala
                85                  90                  95

Lys Tyr Ala Gly Gly Tyr Ser Ile Asp Ala Trp Gly His Gly Thr Glu
            100                 105                 110

Val Ile Val Ser Ser
        115


<210> SEQ ID NO 4
<211> LENGTH: 104
<212> TYPE: PRT
<213> ORGANISM: Artificial Sequence
<220> FEATURE:
<223> OTHER INFORMATION: ANTI-[TRISP][C9] VL

<400> SEQUENCE: 4

Ala Leu Thr Gln Pro Ser Ser Val Ser Ala Asn Pro Gly Glu Thr Val
1               5                   10                  15

Lys Ile Thr Cys Ser Gly Ser Ser Gly Ser Tyr Gly Trp Tyr Gln Gln
            20                  25                  30

Lys Ser Pro Gly Ser Gly Pro Val Thr Val Ile Tyr Tyr Asn Asp Lys
        35                  40                  45

Arg Pro Ser Asp Ile Pro Ser Arg Phe Ser Gly Ser Ala Ser Gly Ser
    50                  55                  60

Thr Ala Thr Leu Thr Ile Thr Gly Val Gln Ala Glu Asp Glu Ala Val
65                  70                  75                  80

Tyr Phe Cys Gly Gly Tyr Asp Ser Ser Thr Tyr Val Gly Ile Phe Gly
                85                  90                  95

Ala Gly Thr Thr Leu Thr Val Leu
            100


<210> SEQ ID NO 5
<211> LENGTH: 122
<212> TYPE: PRT
<213> ORGANISM: Artificial Sequence
```

-continued

```
<220> FEATURE:
<223> OTHER INFORMATION: ANTI-[TRISP][18H1] VH

<400> SEQUENCE: 5

Gln Val Gln Leu Lys Glu Ser Gly Pro Gly Leu Val Gln Pro Ser Gln
1               5                   10                  15

Thr Leu Ser Leu Thr Cys Thr Val Ser Gly Leu Ser Leu Thr Ser Asn
            20                  25                  30

Ser Val Gly Trp Ile Arg Gln Pro Pro Gly Lys Gly Leu Glu Trp Met
        35                  40                  45

Gly Ile Ile Trp Ser Asn Gly Gly Thr Asp Tyr Asn Ser Ala Ile Lys
    50                  55                  60

Ser Arg Leu Ser Ile Ser Arg Asp Thr Ser Lys Ser Gln Val Phe Leu
65                  70                  75                  80

Lys Met His Ser Leu Gln Thr Glu Asp Thr Ala Met Tyr Phe Cys Ala
                85                  90                  95

Arg Gly Pro Tyr Tyr Gly Ser Tyr Arg Leu Gly Tyr Phe Asp Tyr Trp
            100                 105                 110

Gly Gln Gly Val Met Val Thr Val Ser Ser
        115                 120


<210> SEQ ID NO 6
<211> LENGTH: 113
<212> TYPE: PRT
<213> ORGANISM: Artificial Sequence
<220> FEATURE:
<223> OTHER INFORMATION: ANTI-[TRISP][18H1] VL

<400> SEQUENCE: 6

Asp Val Val Met Thr Gln Ser Pro Ser Ser Leu Ala Val Ser Ala Gly
1               5                   10                  15

Glu Thr Val Thr Leu Asn Cys Gln Ser Ser Gln Ser Leu Leu Tyr Ser
            20                  25                  30

Gly Thr Gln Asn Asn Tyr Leu Ala Trp Tyr Gln Gln Lys Pro Gly Gln
        35                  40                  45

Ser Pro Lys Leu Leu Ile Ser Trp Ala Ser Thr Arg Gln Ser Gly Val
    50                  55                  60

Pro Leu Arg Phe Ile Gly Ser Gly Ser Gly Thr Asp Phe Thr Leu Thr
65                  70                  75                  80

Ile Thr Ser Val Gln Ala Glu Asp Leu Ala Ile Tyr Tyr Cys Gln Gln
                85                  90                  95

Phe Tyr Asp Thr Pro Leu Thr Phe Gly Ser Gly Thr Lys Leu Glu Ile
            100                 105                 110

Lys
```